US012629533B2

(12) United States Patent
    Woods et al.

(10) Patent No.:     US 12,629,533 B2
(45) Date of Patent:        May 19, 2026

(54) SYSTEM AND METHOD FOR PRECISION DOSING FOR ELECTRICAL STIMULATION OF THE BRAIN

(71) Applicant: UNIVERSITY OF FLORIDA RESEARCH FOUNDATION, INCORPORATED, Gainesville, FL (US)

(72) Inventors: Adam J. Woods, Gainesville, FL (US); Alejandro Albizu, Gainesville, FL (US); Ruogu Fang, Gainesville, FL (US); Aprinda Indahlastari, Alachua, FL (US)

(73) Assignee: UNIVERSITY OF FLORIDA RESEARCH FOUNDATION, INCORPORATED, Gainesville, FL (US)

( * ) Notice:    Subject to any disclaimer, the term of this patent is extended or adjusted under 35 U.S.C. 154(b) by 423 days.

(21) Appl. No.:    18/018,734

(22) PCT Filed:    Jul. 28, 2021

(86) PCT No.:    PCT/US2021/043495
     § 371 (c)(1),
     (2) Date:    Jan. 30, 2023

(87) PCT Pub. No.: WO2022/026573
     PCT Pub. Date: Feb. 3, 2022

(65)         Prior Publication Data
     US 2023/0293899 A1      Sep. 21, 2023

Related U.S. Application Data

(60) Provisional application No. 63/057,447, filed on Jul. 28, 2020.

(51) Int. Cl.
     *A61N 1/40*      (2006.01)
     *A61N 1/36*      (2006.01)
(52) U.S. Cl.
     CPC ........... *A61N 1/40* (2013.01); *A61N 1/36025* (2013.01); *A61N 1/36082* (2013.01)
(58) Field of Classification Search
     None
     See application file for complete search history.

(56)         References Cited

U.S. PATENT DOCUMENTS 5,452,407 A    9/1995  Crook
     7,412,276 B2   8/2008  Halperin et al.
              (Continued)

OTHER PUBLICATIONS

Morey, Rajendra A. et al., "A comparison of automated segmentation and manual tracing for quantifying hippocampal and amygdala volumes", Neuroimage, Apr. 15, 2009, vol. 45, No. 3, pp. 855-866.
         (Continued)

*Primary Examiner* — Michael W Kahelin
(74) *Attorney, Agent, or Firm* — Timothy H. Van Dyke; Wolter Van Dyke Davis, PLLC

(57)         ABSTRACT
A method is provided for precision dosing of electrical stimulation of the brain. The method includes determining a location of each voxel of a plurality of voxels in a reference frame of an electro-stimulation device including a plurality of electrodes positioned on a head of a subject. The method also includes obtaining measurements that indicate a tissue type at each voxel inside the head of the subject based on an imaging device. The method also includes determining, with a processor, a value of one or more parameters of the electro-stimulation device based on the tissue type measurements at each voxel such that the electro-stimulation device is configured to generate a value of one or more parameters of an electric field at each voxel inside the head of the subject to improve the treatment outcome of the subject.

24 Claims, 16 Drawing Sheets

(56) References Cited

U.S. PATENT DOCUMENTS

| | | | |
|---|---|---|---|
| 7,860,548 B2 | 12/2010 | McIntyre et al. | |
| 2009/0099623 A1* | 4/2009 | Bentwich | A61N 1/36025 |
| | | | 607/45 |
| 2012/0265261 A1 | 10/2012 | Bikson et al. | |
| 2016/0228702 A1* | 8/2016 | Kempe | A61N 1/0476 |
| 2018/0345006 A1* | 12/2018 | Ambrose | A61B 5/0536 |

OTHER PUBLICATIONS

Mwangi, Benson et al., "A review of feature reduction techniques in neuroimaging", Neuroinformatics, Apr. 2014, vol. 12, No. 2, pp. 229-244.

Nissim, Nicole R. et al., "Effects of Transcranial Direct Current Stimulation Paired With Cognitive Training on Functional Connectivity of the Working Memory Network in Older Adults", Frontiers in Aging Neuroscience, Dec. 2019, vol. 11, article 340, 11 pages.

Nitsche, M.A. et al., "Excitability changes induced in the human motor cortex by weak transcranial direct current stimulation", Journal of Physiology, 2000, vol. 537, No. 3, pp. 633-639.

Nitsche, Michael A. et al., "Transcranial direct current stimulation: State of the art 2008", Brain Stimulation, 2008, vol. 1, pp. 206-223.

Oostenveld, Robert et al., "The five percent electrode system for high-resolution EEG and ERP measurements", Clinical Neurophysiology, 2001, vol. 112, pp. 713-719.

Opitz, Alexander et al., "On the importance of precise electrode placement for targeted transcranial electric stimulation", Neuroimage, Nov. 1, 2018, vol. 181, pp. 560-567.

Packard, Mark G. et al., "Learning and memory functions of the Basal Ganglia", Annu. Rev. Neurosci., 2002, vol. 25, pp. 563-593.

Petrides, Michael, "Dissociable role of mid-dorso; ateral prefrontal and anterior inferotemporal cortex in visual working memory", The Journal of Neuroscience, Oct. 1, 2000, vol. 20, No. 19, pp. 7496-7503.

Podda, Maria Vittoria et al., "Anodal transcranial direct current stimulation boosts synaptic plasticity and memory in mice via epigenetic regulation of Bdnf expression", Scientific Reports, 2016, vol. 6, No. 22180, 19 pages.

Polosecki, Pablo et al., "Resting-state connectivity stratifies premanifest Huntington's disease by longitudinal cognitive decline rate", Scientific Reports, 2020, vol. 10, No. 1252, 16 pages.

Qianqian Fang et al., "Tetrahedral Mesh Generation From Volumetric Binary and Grayscale Images", IEEE, 2009, 4 pages.

Radman, Thomas et al., "Role of cortical cell type and morphology in sub- and suprathreshold uniform electric field stimulation", Brain Stimmul., Oct. 1, 2009, vol. 2, No. 4, pp. 215-228.

Ranieri, F. et al., "Modulation of LTP at rat hippocampal CA3-CA1 synapses by direct current stimulation", J Neurophysiol, 2012, vol. 107, pp. 1868-1880.

Rawji, Vishal et al., "tDCS changes in motor excitability are specific to orientation of current flow", Brian Stimulation, 2018, vol. 11, pp. 289-298.

Rosen, Allyson C. et al., "Noninvasive transcranial brain stimulation and pain", Curr Pain Headache Rep., Feb. 2009., vol. 13, No. 1, pp. 12-17.

Sadleir, Rodalind J. et al., "Target optimization in transccranial direct current stimulation", Frontiers in Psychiatry, 2012, vol. 3, article 90, 13 pages.

Saeys, Yvan et al., A review of feature selection techniques in bioinformatics, Oxford University Press, 2005, 11 pages.

Shinde A. B. et al., "Identifying the engagement of a brain network during a targeted tDCS-fMRI experiment using a machine learning approach", bioRxiv preprint doi: https://doi.org/10.1101/2022.09.12.507591; this version posted Jan. 24, 2023.

Smirnov, N., "Table for estimating the goodness of fit of empirical distributions", The Annals of Mathematical Statistics, 1948, https://doi.org/10.1214/aoms/1177730256.

Sue, Paulo J.C. et al., "Association between tDCS computational modeling and clinical outcomes in depression: data from the Elect-TDCS trial", Eur Arch Psychiatry Clin Neurosci. Feb. 2021, vol. 271, No. 1, pp. 101-110.

Szymkowicz, Sarah M. et al., "Transcranial Direct Current Stimulation Use in the Treatment of Neuropsychiatric Disorders: A Brief Review", Psychiatr Ann. Nov. 2016, vol. 46, No. 11, pp. 642-646.

Truong, Dennis Q. et al., "Computational modeling of transcranial direct current stimulation (tDCS) in obesity: Impact of head fat and dose guidelines", NeuroImage: Clinical, 2013, vol. 2, pp. 759-766.

Valente, Giancarlo et al., "Cross-validation and permutations in MVPA: Validity of permutation strategies and power of cross-validation schemes", NeuroImage, 2021, vol. 238, 14 pages.

Windhoff, Mirko et al., "Electric Field Calculations in Brain Stimulation Based on Finite Elements: An Optimized Processing Pipeline for the Generation and Usage of Accurate Individual Head Models", Human Brain Mapping, 2013, vol. 34, pp. 923-935.

Woods, Adam J. et al., "Effects of electrode drift in transcranial direct current stimulation", Brain Stimul., 2015, vol. 8, No. 3, pp. 515-519.

Woods, AJ et al., "A technical guide to tDCS, and related noninvasive brain stimulation tools", Clin Neurophysiol., Feb. 2016, vol. 127, No. 2, pp. 1031-1048.

Woods, Adam J. et al., "Augmenting cognitive training in older adults (The ACT Study): Design and Methods of a Phase III tDCS and cognitive training trial", Contemp Clin Trials, Feb. 2018, vol. 65, pp. 19-32.

PCT Search Report & Written Opinion, PCT/US2021/043495, mailed Dec. 17, 2021, 10 pages.

Albizu, Alejandro et al., "Machine-learning defined precision tDCS for improving cognitive function", Brian Stimulation, 2023, vol. 16, pp. 969-974.

Albizu, Alejandro et al., "Machine learning and individual variability in electric field characteristics predict tDCS treatment response", Brian Stimulation, 2020, vol. 13, pp. 1753-1764.

Antonenko, Daria et al., "Towards precise brain stimulation: Is electric field simulation related to neuromodulation?" Brain Stimulation, 2018, 11 pages.

Ashburner, John, "A fast diffeomorphic image registration algorithm", NeuroImage, 2007, vol. 38, pp. 95-113.

Bikson, Marom et al., "Safety of transcranial direct current stimulation: Evidence based update 2016", Brain Stimul., 2016, vol. 9, No. 5, pp. 641-661.

Blumenfeld, Robert S. et al., "Lateral Prefrontal Cortex is Organized into Parallel Dorsal and Ventral Streams Along the Rostro-Caudal Axis", Cerebral Cortex, 2012, 11 pages.

Cardinale, Francesco et al., "Validation of FreeSurfer-Estimated Brain Cortical Thickness: Comparison with Histologic Measurements", Neuroinform, 2014, 9 pages.

Chang, Chih-Chung et al., LIBSVM: A library for support vector machines, Department of Computer Science, Aug. 23, 2022, 40 pages.

Chhatbar, Pratik Y. et al., "Transcranial direct current stimulation post-stroke upper extremity motor recovery studies exhibit a dose-response relationship", Brain Stimul., 2016, vol. 9, No. 1, pp. 16-26.

Clancy, Kevin J. et al., "Intrinsic sensory disinhibition contributes to intrusive reexperiencing in combat veterans", Scientific Reports, 2020, vol. 10, No. 936, 11 pages.

Clancy, Kevin J. et al., "Lasting connectivity increase and anxiety reduction via transcranial alternating current stimulation", Social Cognitive and Affective Neuroscience, 2018, pp. 1305-1316.

Cole, James H. et al., "Prediction of brain age suggests accelerated atrophy after traumatic brain injury", Ann Neurol, 2015, vol. 77, pp. 571-581.

Datta, Abhishek et al., "Gyri—precise head model of transcranial DC stimulation: Improved spatial focality using a ring electrode versus conventional rectangular pad", Brain Stimul., Oct. 1, 2009, vol. 2, No. 4, pp. 201-207.

Datta, Abhishek et al., "Individualized model predicts brain current flow during transcranial direct-current stimulation treatment in responsive stroke patient", Brain Stimul. Jul. 2011, vol. 4, No. 3, pp. 169-174.

(56)                    References Cited

OTHER PUBLICATIONS

D'Esposito, M. et al., "Maintenance versus Manipulation of Information Held in Working Memory: An Event-Related fMRI Study", Brain and Cognition, 1999, vol. 41, pp. 66-86.

Dmochowski, Jacek P. et al., "The Point Spread Function of the Human Head and its Implications for Transcranial Current Stimulation", Phys Med Biol. Oct. 21, 2012, vol. 57, No. 20, pp. 6459-6477.

Dmochowski, Jacek P. et al., "Optimized multi-electrode stimulation increases focality and intensity at target", Journal of Neural Engineering, Jun. 2011, vol. 8, 16 pages.

Dmochowski, Jacek P. et al., "Targeted Transcranial Direct Current Stimulation for Rehabilitation after Stroke", Neuroimage, Jul. 15, 2013, vol. 75, pp. 12-19.

Dunois, Julien et al., "Resting-state functional brain connectivity best predicts the personality dimension of openness to expience", Personality Neuroscience, 2018, vol. 1, pp. 1-21.

Esmaeilpour, Zeinab et al., "Incomplete evidence that increasing current intensity of tDCS boots outcomes", Brain Stimul. 2018, vol. 11, No. 2, pp. 310-321.

Fawcett, Tom, "ROC Graphs: Notes and Practical Considerations for Data Mining Researchers", HP Laboratories, 2003, 28 pages.

Fritsch, Brita et al., "Direct current stimulation promotes BDNF-dependent synaptic plasticity: Potential implications for motor learning", Neuron. Apr. 29, 2010, vol. 66, No. 2, pp. 198-204.

Gabriel, S. et al., "The dielectric properties of biological tissues: II. Measurements in the frequency range 10 Hz to 20 GHz", Phys. Med. Biol., 1996, vol. 41, pp. 2251-2269.

Göksu, Cihan et al.,"Human in-vivo brain magnetic resonance current density imaging (MRCDI)", NeuroImage, 2018, 40 pages.

Guyon, I. et al., "Automatic capacity tuning of a very large VC-dimension classifiers", Adv Neural Inf Process Syst, 1993, 9 pages.

Guyon, Isabelle et al., "An Introduction to Variable and Feature Selection", Journal of Machine Learning Research, 2003, vol. 3, pp. 1157-1182.

Hausman, Hanna K. et al., "The Role of Resting-State Network Functional Connectivity in Cognitive Aging", Front. Aging Neurosci., 2020, vol. 12, No. 177, 10 pages.

Huang, Yu et al., "Measurements and models of electric fields in the in vivo human brain during transcranial electric stimulation", eLife, 2017, 26 pages.

Huang, Yu et al., "Optimized tDCS for Targeting Multiple Brain Regions: An Integrated Implementation", n.d.

Huang, Yu et al., "Realistic volumetric-approach to simulate transcranial electric stimulation—Roast—a fully automated open-source pipeline", J Neural Eng., Jul. 30, 2020, vol. 16, No. 5, 26 pages.

Huang, Yu et al., "Automated MRI Segmentation for Individualized Modeling of Current Flow in the Human Head", J Neural Eng., Dec. 2013, vol. 10, No. 6, 26 pages.

Indahlastari, Aprinda et al., "Methods to monitor accurate and consistent electrode placement in conventional transcranial electrical stimulation", Brain Stimul., 2019, vol. 12, No. 2, pp. 267-274.

Indahlastari, Aprinda et al., "Methods to Compare Predicted and Observed Phosphene Experience in tACS Subjects", Neural Plasticity, vol. 2018, article ID 8525706, 10 pages.

Indahlastari, Aprinda et al., "Modeling Transcranial Electrical Stimulation in the Aging Brain", Brain Stimul., 2020, vol. 13, No. 3, pp. 664-674.

Kambeitz, Joseph et al., "Clinical patterns differentially predict response to transcranial direct current stimulation (tDCS) and escitalopram in major depression: A machine learning analysis of the Elect-TDCS study", Journal of Affective Disorders, Mar. 2020, vol. 265, pp. 460-467.

Kasinadhuni, A. K. et al., "Imaging of Current Flow in the Human Head During Transcranial Electrical Therapy", Brain Stimul., 2017, vol. 10, No. 4, pp. 764-772.

Kessler, Sudha Kilaru et al., "Dosage Considerations for Transcranial Direct Current Stimulation in Children: A Computational Modeling Study", PLoS ONE, 2013, vol. 8, No. 9, 15 pages.

Khan, Asad et al., "Can individually targeted and optimized multi-channel tDCS outperform standard bipolar tDCS in stimulating the primary somatosensory cortex?", Brain Stimulation, 2023, vol. 16, pp. 1-16.

Kim, Sangha et al., "Predictions of tDCS treatment response in PTSD patients using EEG based classification", Front. Psychiatry, 2022, 10 pages.

Krause, Matthew R. et al., "Transcranial Direct Current Stimulation Facilitates Associative Learning and Alters Functional Connectivity in the Primate Brain", Current Biology, 2017, vol. 27, pp. 3086-3096.

Kronberg, Greg et al., "Direct current stimulation modulates LTP and LTD: activity dependence and dendritic effects", Brain Stimul., 2017, vol. 10, No. 1, pp. 51-58.

Kronberg, Greg et al., "Direct current stimulation boosts hebbian plasticity in vitro", Brain Stimulation, 2020, vol. 13, pp. 287-301.

Li, Jingwei et al., "Global Signal Regression Strengthens Association between Resting-State Functional Connectivity and Behavior", Neuroimage, Aug. 1, 2019, vol. 196, pp. 126-141.

Lindquist, Martin A. et al., "Group-regularized individual prediction: Theory and application to pain", Neuroimage, Jan. 15, 2017, vol. 145(Pt B), pp. 274-287.

Marquez-Ruiz, Javier et al., "Transcranial direct-current stimulation modulates synaptic mechanisms involved in associative learning in behaving rabbits", PNAS, Apr. 24, 2012, vol. 109, No. 17, pp. 6710-6715.

McCann, Hannah et al., "Variation in Reported Human Head Tissue Electrical Conductivity Values", Brain Topography, 2019, vol. 32, pp. 825-858.

McNab, Fiona et al., "Prefrontal cortex and basal ganglia control access to working memory", Nature Neuroscience, Jan. 2008, vol. 11, No. 1, pp. 103-107.

Mercer, J. et al., "XVI. Functions of positive and negative type, and their connection with the theory of Integral Equations", Gott. Nachr., 1904, pp. 415-446.

Minhas, Preet et al., "Transcranial Direct Current Stimulation in Pediatric Brain: A computational modeling study", Conf Proc IEEE Eng Med Biol Soc., 2012, pp. 859-862.

* cited by examiner 110 2-D SCAN 112
2D SCAN ELEMENTS
(PIXELS)

102
X DIRECTION

104
Y DIRECTION

124

104

106
Z DIRECTION 122
3D SCAN ELEMENTS
(VOXELS)

102

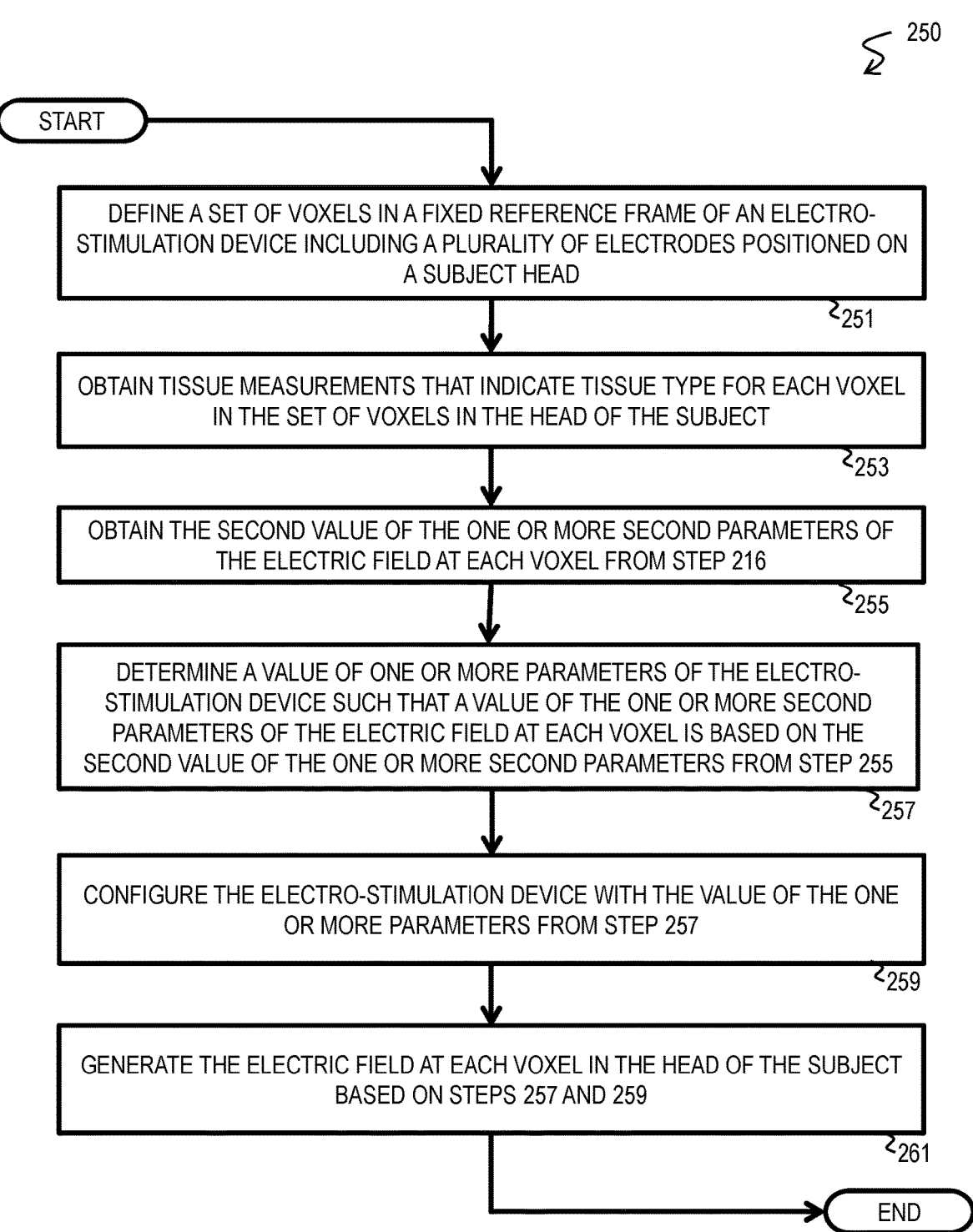

250

START

DEFINE A SET OF VOXELS IN A FIXED REFERENCE FRAME OF AN ELECTRO-STIMULATION DEVICE INCLUDING A PLURALITY OF ELECTRODES POSITIONED ON A SUBJECT HEAD

251

OBTAIN TISSUE MEASUREMENTS THAT INDICATE TISSUE TYPE FOR EACH VOXEL IN THE SET OF VOXELS IN THE HEAD OF THE SUBJECT

253

OBTAIN THE SECOND VALUE OF THE ONE OR MORE SECOND PARAMETERS OF THE ELECTRIC FIELD AT EACH VOXEL FROM STEP 216

255

DETERMINE A VALUE OF ONE OR MORE PARAMETERS OF THE ELECTRO-STIMULATION DEVICE SUCH THAT A VALUE OF THE ONE OR MORE SECOND PARAMETERS OF THE ELECTRIC FIELD AT EACH VOXEL IS BASED ON THE SECOND VALUE OF THE ONE OR MORE SECOND PARAMETERS FROM STEP 255

257

CONFIGURE THE ELECTRO-STIMULATION DEVICE WITH THE VALUE OF THE ONE OR MORE PARAMETERS FROM STEP 257

259

GENERATE THE ELECTRIC FIELD AT EACH VOXEL IN THE HEAD OF THE SUBJECT BASED ON STEPS 257 AND 259

261

END

SYSTEM AND METHOD FOR PRECISION DOSING FOR ELECTRICAL STIMULATION OF THE BRAIN

CROSS REFERENCE TO RELATED APPLICATIONS

This application claims priority to U.S. Provisional Application No. 63/057,447 filed 28 Jul. 2020.

STATEMENT OF GOVERNMENTAL INTEREST

This invention was made with government support under Grant Number NIA R01AG054077, NIA K01AG050707 awarded by the National Institutes of Health/National Institute on Aging. The government has certain rights in the invention.

BACKGROUND

Electrical brain stimulation (EBS) has been used to treat clinical conditions and affiliated symptoms for decades (e.g., electroconvulsive therapy, transcranial magnetic stimulation, transcranial direct current stimulation, transcranial alternative current stimulation, transcranial random noise stimulation, deep brain stimulation, etc.). Transcranial direct current stimulation (tDCS) is widely investigated as a therapeutic tool to treat a myriad of clinical conditions and symptoms (e.g., cognitive, physical, etc.). Since nearly two decades ago, tDCS has been instrumental in advancing the knowledge of human brain function by altering neural activity in the brain [1-3]. tDCS has been suggested to alter resting membrane potentials (i.e., modulate or attenuate) to influence neuronal excitability across the local field of stimulation [1-5]. With this, tDCS has shown great promise as a therapeutic intervention in various neurological and psychiatric disorders [6-9]. While the number of tDCS applications within the literature has grown exponentially [1-5], the optimal dosing parameters (e.g., applied current, electrode placement, etc.) that underlie the positive effect of tDCS remain unclear.

SUMMARY

Prior research demonstrates that electric current delivery to the brain can vary significantly across individuals. Quantification of this variability could enable person-specific optimization of EBS outcomes. The embodiments of the present invention used machine learning and Magnetic Resonance Imaging (MRI)-derived electric field models to predict working memory improvements with EBS (e.g. tDCS) as a proof of concept for precision treatment outcome (e.g. cognitive intervention) from electrical brain stimulation.

In a first set of embodiments, a method is provided for precision dosing of electrical stimulation of the brain. The method includes determining a location of each voxel of a plurality of voxels in a reference frame of an electro-stimulation device including a plurality of electrodes positioned on a head of a subject. The method also includes obtaining measurements that indicate a tissue type at each voxel inside the head of the subject based on an imaging device. The method also includes determining, with a processor, a value of one or more parameters of the electro-stimulation device based on the tissue type measurements at each voxel such that the electro-stimulation device is configured to generate a value of one or more parameters of an electric field at each voxel inside the head of the subject to improve a treatment outcome (e.g. cognitive function) of the subject.

In a second set of embodiments, a system is provided for precision dosing of electrical stimulation of the brain. The system includes an electro-stimulation device comprising a plurality of electrodes. The method also includes a processor and a memory including one or more sequences of instructions. The memory and the sequence of instructions are configured to, with the processor, cause the system to determine a location of each voxel of a plurality of voxels in a reference frame of the electro-stimulation device positioned on a head of a subject. The memory and the sequence of instructions are further configured to, with the processor, cause the system to obtain measurements that indicate a tissue type at each voxel inside the head of the subject based on an imaging device. The memory and the sequence of instructions are further configured to, with the processor, cause the system to determine a value of one or more parameters of the electro-stimulation device based on the tissue type measurements at each voxel such that the electro-stimulation device is configured to generate a value of one or more parameters of an electric field at each voxel inside the head of the subject to improve a treatment outcome (e.g. cognitive function) of the subject.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 2B is a block diagram that illustrates an example of a method for determining parameter values of the electro-stimulation device on a subject to achieve improved treatment outcome, according to an embodiment;

3

4

Figure 1A:
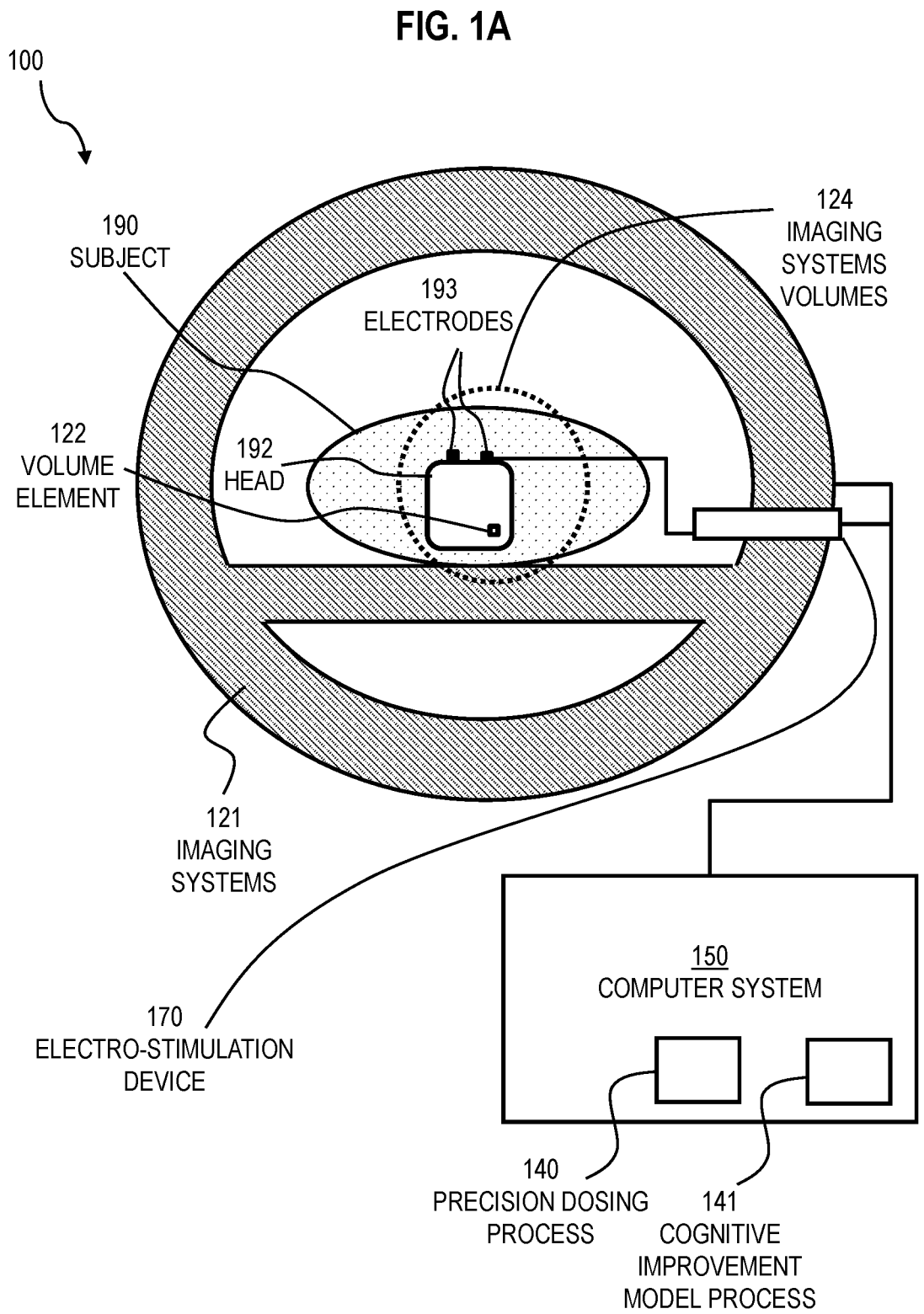
FIG. 1A is a block diagram that illustrates an example system for precision dosing of electrical-stimulation of the brain, according to an embodiment.
Figure 2A:
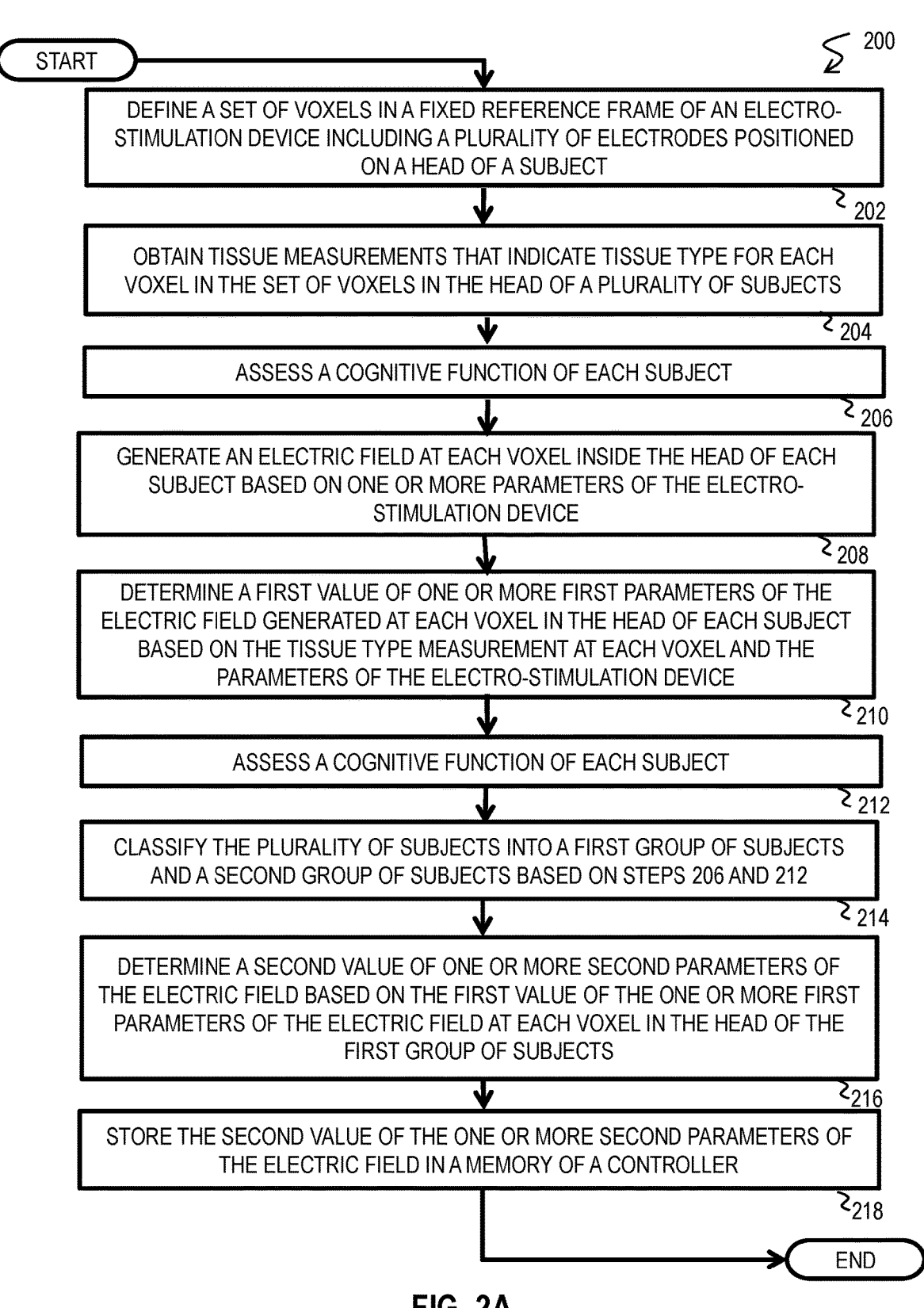
FIG. 2A is a block diagram that illustrates an example of a method to determine parameter values of an electric field within a head of a subject to improve treatment outcome, according to an embodiment.
Figure 3:
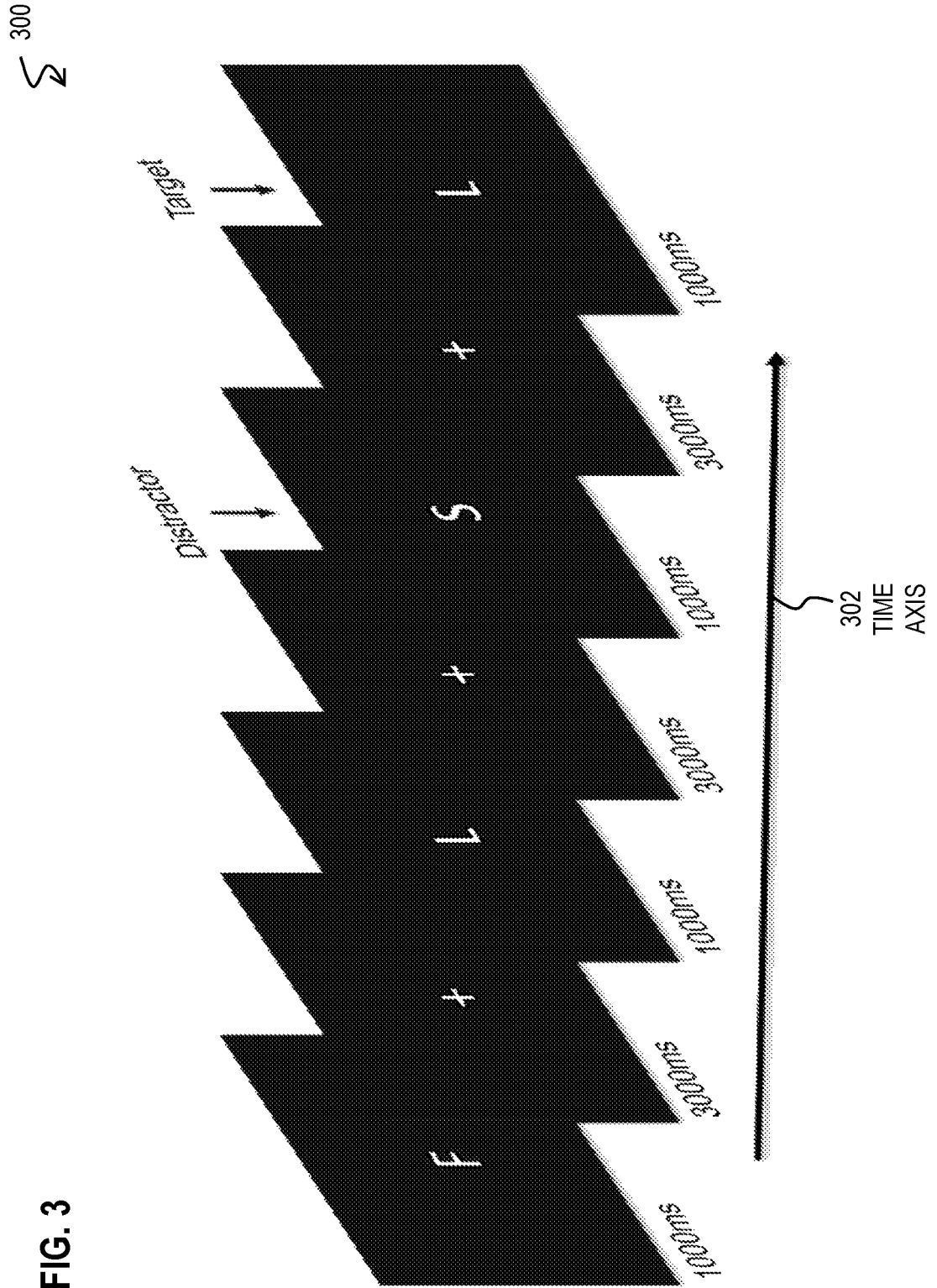
FIG. 3 is an image that illustrates an example of a test to assess a cognitive function of a subject, according to an embodiment.
Figure 4A:
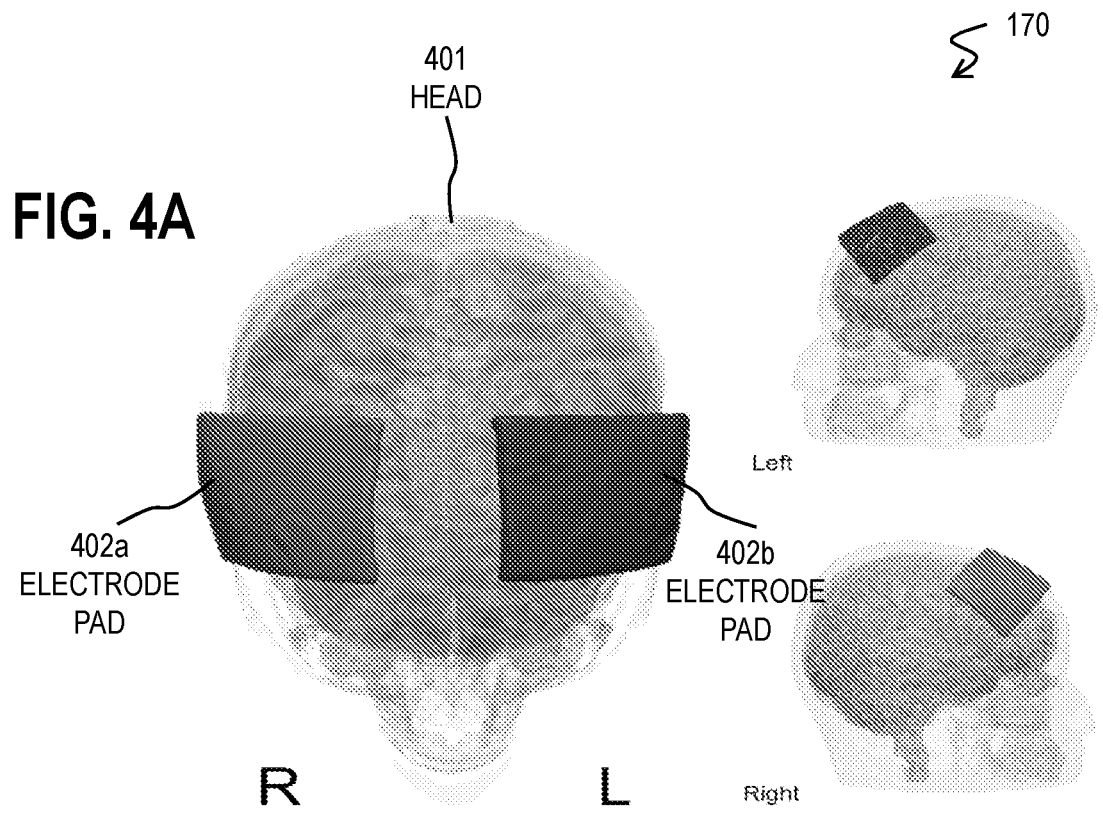
FIG. 4A is an image that illustrates an example of electrode pads of the electro-stimulation device of FIG. 1A positioned on a head of a subject, according to an embodiment.
Figure 4B:
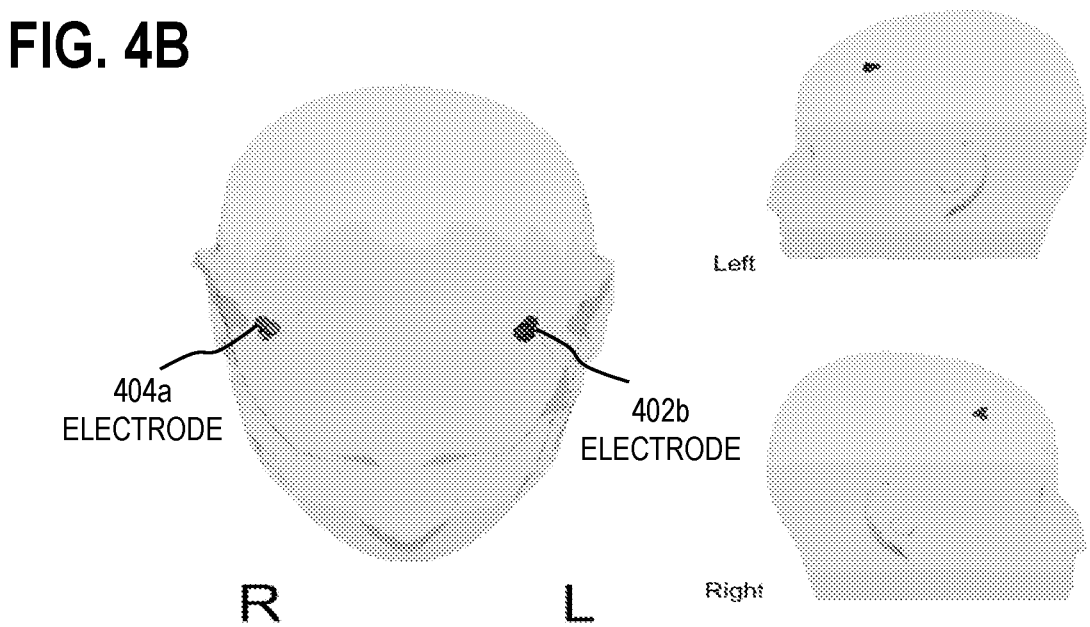
Figures 5A, 5B:
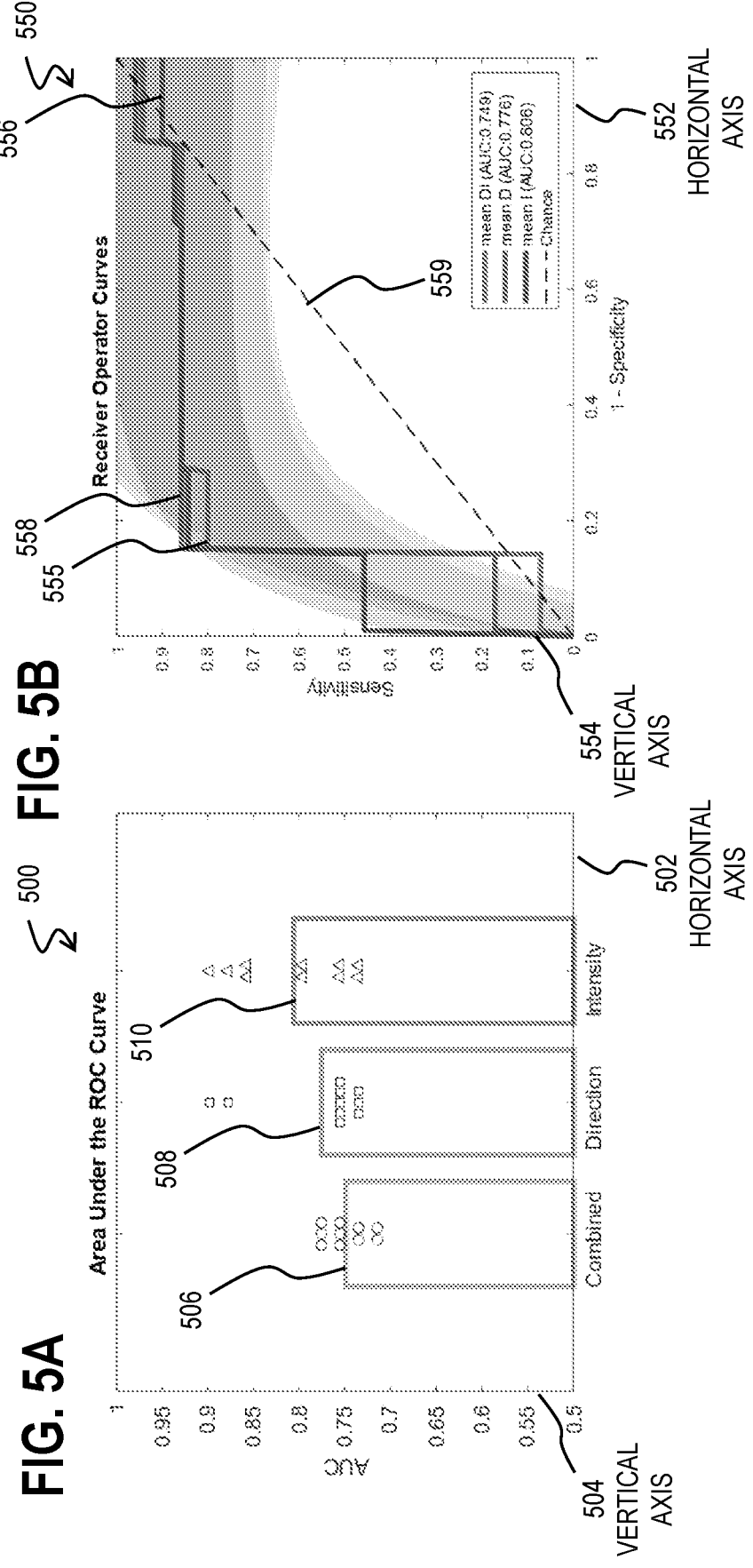
Figure 6:
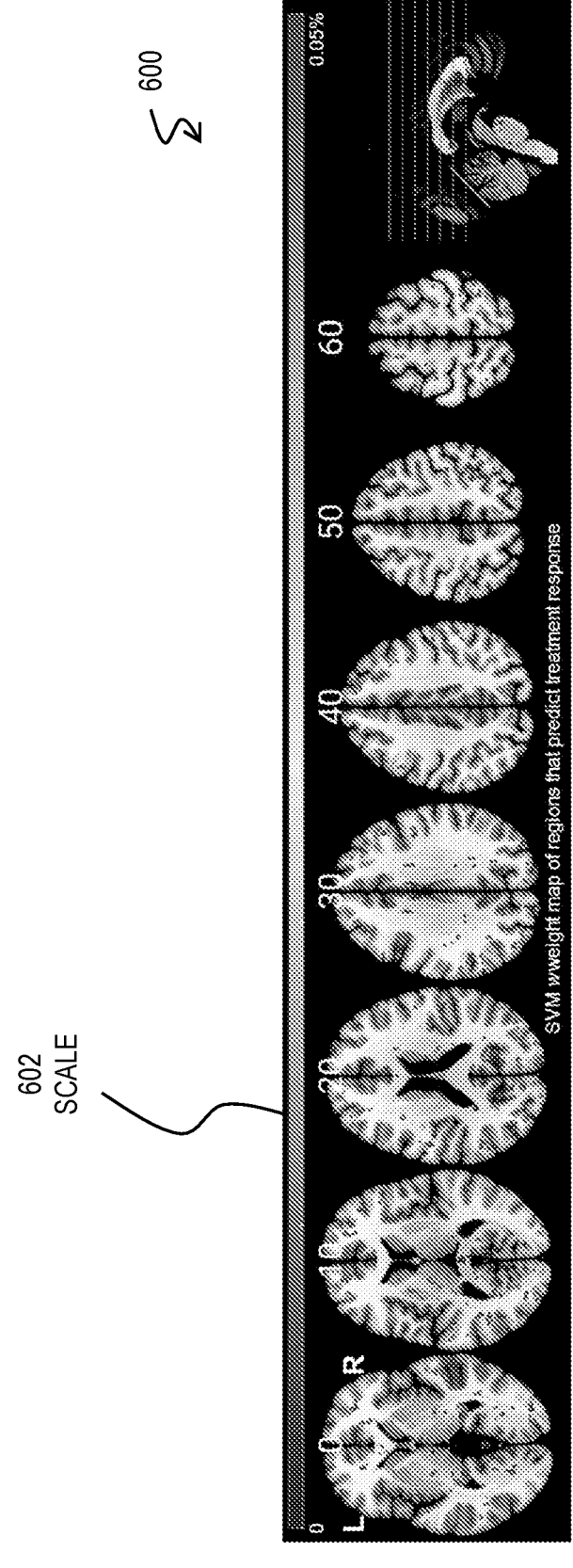
Figures 8A, 8B, 8C, 8D:
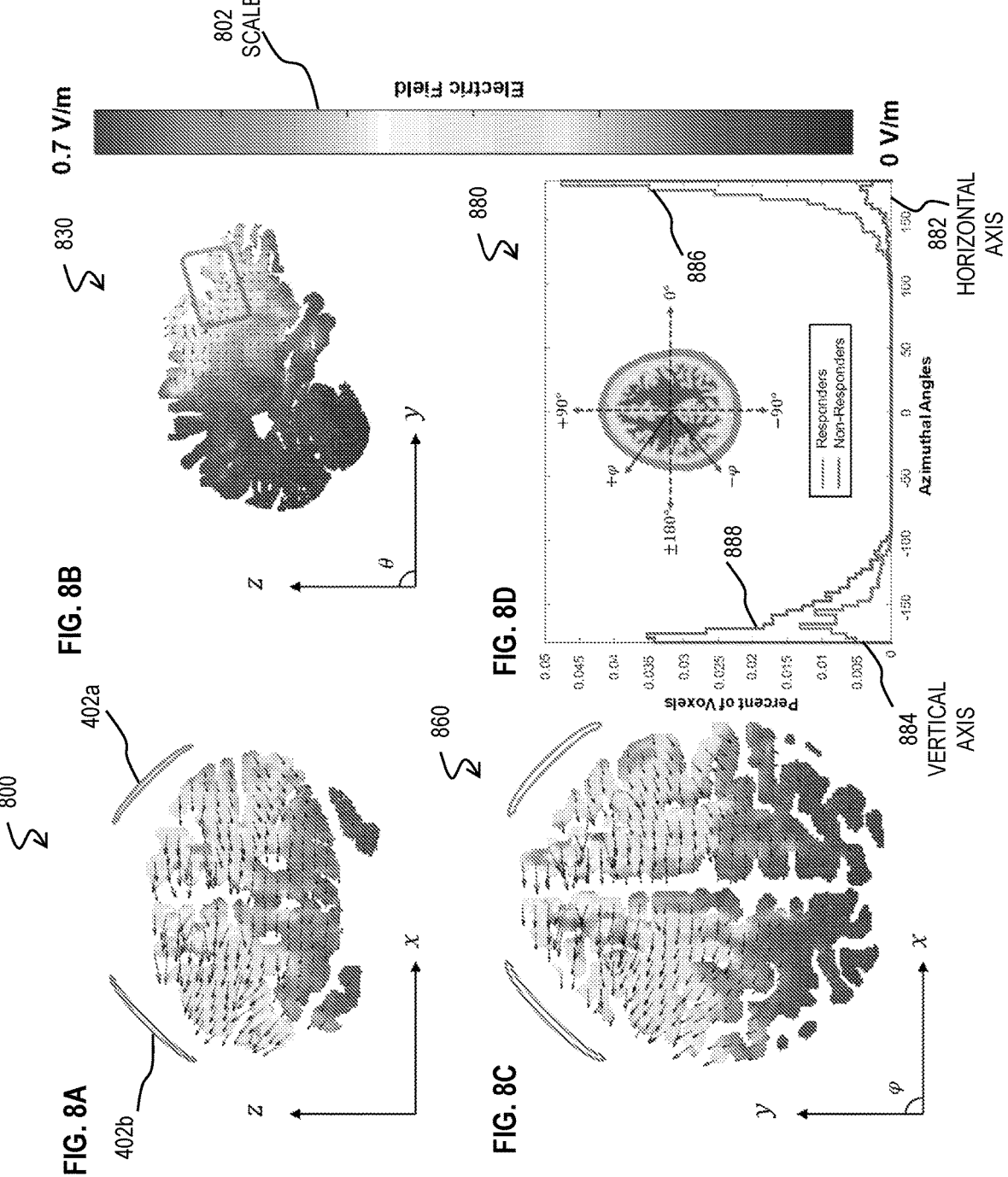
Figures 9A, 9B:
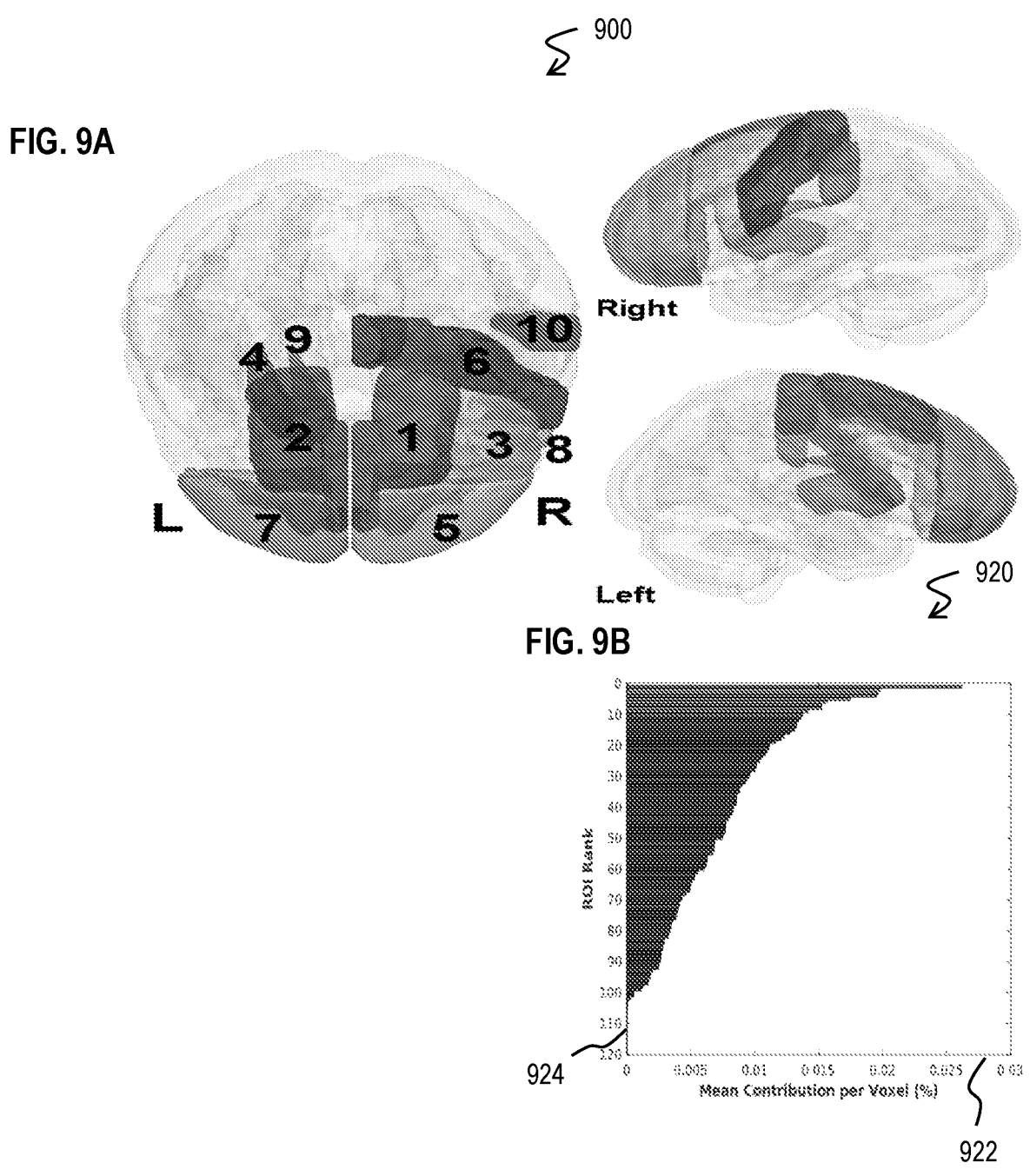
Figure 13:
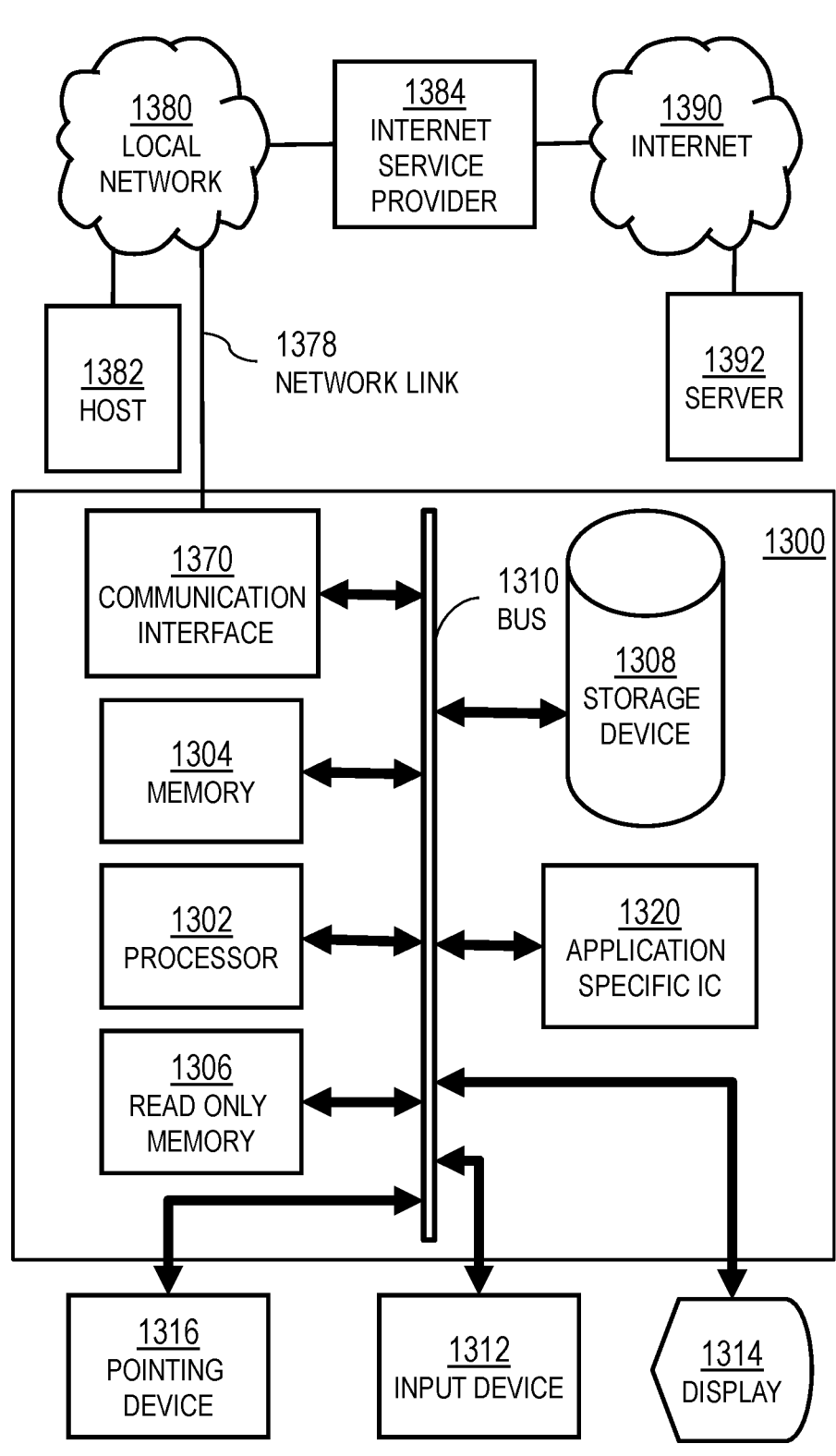
Figure 14:
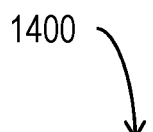
Figure 14:
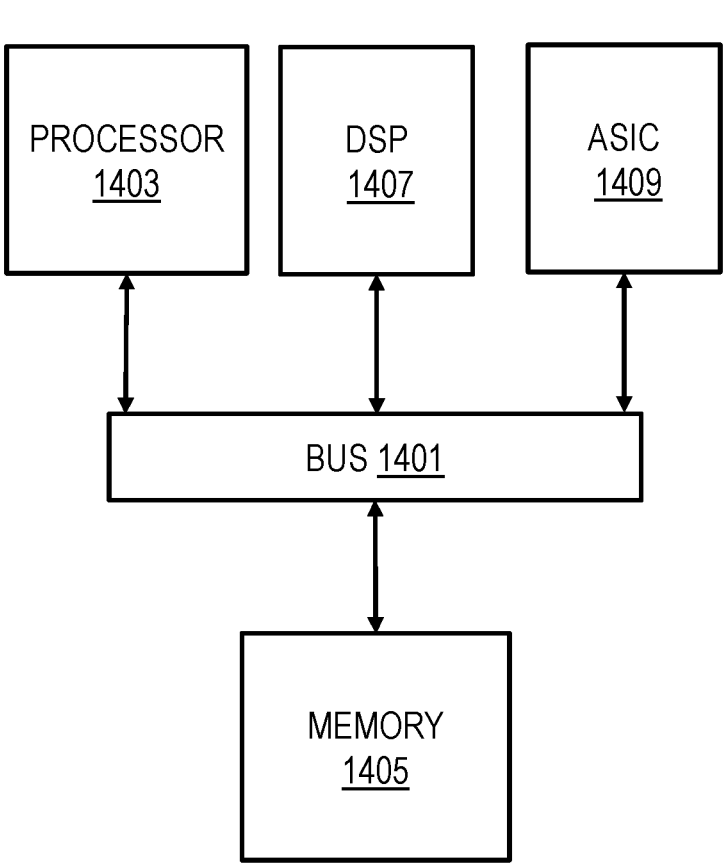

FIG. 4B is an image that illustrates an example of electrodes of the electro-stimulation device of FIG. 1A positioned on a head of a subject, according to an embodiment;

FIG. 5A is an image that illustrates an example of a histogram depicting the area under the receiver operating curve (ROC) of FIG. 5B for different parameters of the electric field to predict an outcome of the cognitive test of FIG. 3, according to an embodiment;

FIG. 5B is an image that illustrates an example of ROC curves to predict an outcome of the cognitive test of FIG. 3 for multiple subjects based on different parameters of the electric field, according to an embodiment;

FIG. 6 is an image that illustrates an example of multiple discrimination maps that indicate a contribution of each voxel to distinguish groups of subjects based on an outcome of the cognitive test of FIG. 3, according to an embodiment;

FIGS. 7A through 7D are graphs that illustrate parameter values of the electric field generated in the head of multiple subjects to predict outcomes of the multiple subjects performing the cognitive test of FIG. 3, according to an embodiment;

FIGS. 8A through 8C are images that illustrate multiple parameter values of the electric field generated in the head of a subject, according to an embodiment;

FIG. 8D is a graph with plots that indicate a ratio of the pixels in the images of FIGS. 8A through 8C based on a direction of the electric field, according to an embodiment;

FIG. 9A are images that illustrate a mean contribution of different regions of the brain of the subject to distinguish groups of subjects based on an outcome of the cognitive test of FIG. 3, according to an embodiment;

FIG. 9B is a histogram that depicts the contribution of different regions of the brain of the subject to distinguish groups of subjects based on an outcome of the cognitive test of FIG. 3, according to an embodiment;

FIGS. 10A through 10D are graphs that illustrate parameter values of displacement of the electrodes of FIG. 1A to predict outcomes of the multiple subjects performing the cognitive test of FIG. 3, according to an embodiment;

FIGS. 11A through 11F are images that depict various steps of the methods of FIGS. 2A and 2B, according to an embodiment;

FIGS. 12A through 12F are images that depict a comparison between conventional fixed dosing and optimized dosing based on the methods of FIGS. 2A and 2B, according to an embodiment;

FIG. 13 is a block diagram that illustrates an example computer system upon which an embodiment of the invention may be implemented; and FIG. 14 is a block diagram that illustrates an example chip set upon which an embodiment of the invention may be implemented.

DETAILED DESCRIPTION

A method and apparatus are described for determining dose characteristics of an electro-stimulation of the brain to improve treatment outcome (e.g. cognitive function). In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of electro-stimulation of the brain for purposes of improving treatment outcome (e.g. cognitive function of the brain). For purposes of this description, "electro-stimulation of the brain" or "electrical brain stimulation" (EBS) means any form of electrical brain stimulation to calculate precision dosing characteristics. This includes, but is not limited to, transcranial magnetic stimulation, electroconvulsive therapy, deep brain stimulation, transcranial direct current stimulation (tDCS), transcranial alternative current stimulation, transcranial random noise stimulation, deep brain stimulation and other forms of transcranial electrical stimulation.

In addition, while the proof of concept presented specifically targeted cognitive function, this approach can also be applied in the context of any "outcome measure" affiliated with treatment response or treatment outcome. In one embodiment, the outcome measure is affiliated with a cognitive function. In another embodiment, the outcome measure is affiliated with one or more of a physical condition, a mental health condition, neuroimaging, aging and/or treatment for one or more medical conditions associated with a physical or mental health condition (e.g. Alzheimer's). In some embodiments, the invention is described in the context of transcranial direct current stimulation (tDCS). In still other embodiments, the invention is described in the context of using electric field characteristics to predict EBS (e.g. tDCS) treatment response. In still other embodiments, the invention is described in the context of assessing how current intensity and direction play significant roles in EBS (e.g. tDCS) treatment response. In still other embodiments, the invention is described in the context of assessing how voxel-wise current characteristics predict EBS (e.g. tDCS) treatment response (e.g. with 86% accuracy). In still other embodiments, the invention is described in the context of how current intensity yields the best overall machine learning classifier of EBS (e.g. tDCS) response. In still other embodiments, the invention is described in the context of assessing how precision dosing which accounts for individual anatomy may be used to optimize EBS (e.g. tDCS). While the proof of concept presented here is for tDCS, these methods can be applied with any form of EBS to calculate precision dosing characteristics.

1. Transcranial Direct Current Stimulation

Prior research shows that increasing or decreasing the intensity of applied stimulation to the scalp results in corresponding changes in the electric field within the brain [10]. In vitro studies have shown that the intensity component of tDCS current can modulate cortical excitability [11,12]. Experimental and theoretical studies have indicated that tDCS-related electric field intensity is essential for altering neuron resting membrane potentials and modification of synaptic strength (i.e., LTP/LTD) [13-17]. Studies show that increased applied current intensity is associated with increased amplitude of motor evoked potentials (MEPs), suggesting neuronal sensitization of the motor cortex [8,18-20]. Therefore, varying levels of applied current intensity in tDCS may lead to changes in behavioral outcomes.

Furthermore, electrode placements during tDCS can greatly affect the distribution and direction of electric current throughout the brain [21,22]. Whole-cell recordings have demonstrated that electric field orientation is essential to the likelihood of neuronal firing [23]. Neuronal bodies in parallel with the direction of applied electric fields are more susceptible to stimulation responses. Human studies have also highlighted the importance of tDCS current direction for modulating cortical excitability [24,25]. Rawji et al. (2018) evaluated individual effects of tDCS montages that produced electric fields oriented orthogonal or parallel to the motor cortex on the modulation of MEPs. The orthogonal montage was observed to have greater current flow normal to the cortical surface (i.e., current flow in parallel with the dendritic axis of cortical neurons). These authors reported significant alterations in MEPs with this montage compared to sham [25]. The inventors of the present invention recognized that based on this data, the direction of current flow in the tDCS electric field may be strongly correlated with behavioral outcomes of tDCS.

Conventional tDCS typically employs a fixed applied current (e.g., 2 mA) and electrode placement (e.g., F3/F4) across participants [26]. However, the orientation and intensity of the generated electric field within cortical tissue can be dramatically altered by inter-individual anatomical differences. For instance, brain atrophy can reduce the level of current reaching the brain due to an increase in current shunting within cerebrospinal fluid (CSF) [27,28]. Individual skull thickness and subcutaneous adipose tissue volume can also alter voltage delivery due to differences in tissue conductivity [29-32].

MRI-derived finite element models (FEM) can be used to estimate individualized electric field induced by tDCS. Advancements in tissue segmentation tools and automated modeling pipelines [33,34] have enabled more efficient generation of large and complex FEM that would normally require extensive computing power and time. These models have recently been compared to experimental results obtained via a novel in-vivo magnetic resonance electrical impedance tomography technique [35,36] and intracranial recordings [22,37]. While the experimental results showed a strong correlation with computational model outcomes, a large variation across individuals were observed. Therefore, investigating the nuance of electrical distribution in individualized models may provide more insight into inter-individual variability seen with tDCS. However, the size (i.e., millions of voxels across multiple dimensions) and complexity of generated electric fields has made interpretation of the essential current characteristics (i.e., current direction, intensity, etc.) challenging.

Few studies have attempted to systematically investigate these estimates of electric field distributions as a predictor of responses to tDCS [38-40]. All three prior studies reported increases in current intensity associated with increases in the target behavioral response (e.g., self-reported and physiological measures) [38-40]. Antonenko et al. also reported a positive relationship between the current direction normal to the cortical surface and sensorimotor network strength [40]. These studies employed univariate approaches that treat each voxel or region of interest within the brain as an independent predictor of treatment response. The inventors of the present invention recognized that at present, no studies have employed multivariate approaches to investigate patterns within the current distribution as a predictor of treatment response.

Supervised machine learning methods (e.g., support vector machines; SVM) constitute a novel approach in neuroimaging to investigate large and complex datasets [41-44]. SVM uses Mercer's Theorem [45], which allows the representation of high dimensional feature space in a low-dimensional Gram matrix (Equation 4)—also known as the "kernel trick" [46]. SVM performs multivariate analyses across many voxels to classify patterns of information [41] that can be used to identify individual contributions of current intensity and direction towards behavioral responses. Multivariate classifiers are iteratively trained to search for patterns within the data that best predict a specified prognostic label, such as behavioral response. This is usually achieved within a cross-validation procedure, withholding a different partition of data for each iteration of training. This is a standard approach within the statistical literature and a widely used technique to provide unbiased generalizability to new data samples [42-44,47]. Prior studies have used machine-learning of clinical data to predict treatment responses [48]; however, the inventors of the present invention recognized that there are currently no studies that utilize machine learning on FEM to investigate the critical components of dosing parameters in tDCS.

Previous work by the inventors of the present invention demonstrated working memory improvements in older adults following tDCS paired with cognitive training [49]. In the present invention the objective is to apply machine learning and FEM in the same dataset and identify the central determinants of treatment response. Specifically, the present study applied an SVM machine-learning algorithm to investigate the contributions of current intensity and direction, as well as their interaction, for predicting working memory improvements in older adults. The hypothesis of the inventors is that SVM applied to individualized EBS (e.g. tDCS) current models are capable of classifying EBS (e.g. tDCS) responders and non-responders above chance (i.e., area under the curve >0.5). In addition, the inventors hypothesized that the interaction of direction and intensity is the most essential dosing feature for predicting behavioral response. These data will provide critical insight to inform EBS (e.g. tDCS) mechanism theory and provide a potential foundation for methods to increase the effectiveness of EBS (e.g. tDCS) applications.

2. Overview

FIG. 1A is a block diagram that illustrates an example system 100 for precision dosing of electrical-stimulation of the brain, according to an embodiment. For purposes of illustration, a living subject 190 is depicted, but is not part of the system 100. One or more imaging systems 121 are provided, to scan images of the subject 190 within an imaging systems volume 124 that encompasses part of the subject 190 (e.g. at least the head 192). In an example embodiment, the volume 124 may encompass the entire subject 190. In another example embodiment, the volume 124 encompasses a head 192 of the subject 190. The imaging systems 121 are non-invasive and obtain cross-sectional images that are axially stacked to generate imaging data of the volume 124. In an example embodiment, the imaging system 121 is a first imaging device that obtains first measurements that relate to tissue type inside the volume 124. For example, the first imaging device is an X-ray Computed tomography (CT) scanner, a nuclear magnetic resonance imagery (MRI) scanner or a four-dimensional computed tomography (4DCT), or a Single Photon Emission Computed Tomography (SPECT). In an example embodiment, the imaging system 121 obtains structural T1-weighted MRI scans using a 32-channel, receive-only head coil from a 3-tesla Siemens MAGNETOM® Prisma MRI scanner. In this example embodiment, MPRAGE sequence parameters included: repetition time (TR)=1800 ms; echo time (TE)=2.26 ms; flip angle=8°; field of view (FOV)=256×256×176 mm; voxel size=1 mm3.

As illustrated in FIG. 1A, the system 100 includes an electro-stimulation device 170 that includes a plurality of electrodes 193 positioned on a surface of the head 192 of the subject 190. In an embodiment, the electro-stimulation device 170 has one or more parameters including a location of the electrodes 193 on the head 192; a current intensity of the electrodes 193; a duration of stimulation of the head 192 with the electrodes 193; a duration of a ramp up/ramp down of the current intensity; and a number of stimulation sessions. In some embodiments, the locations of the electrodes 193 on the head 192 are based on the 10-20 system. In one embodiment, the electro-stimulation device 170 generates an electric field within the volume 124 (e.g. within the head 192) over a plurality of volume elements or voxels 122 that are defined within a frame of reference of the electro-stimulation device 170. In one embodiment, the electric field generated within each voxel 122 has one or more parameter values (e.g. current intensity, direction, etc.). Although FIG. 1A depicts the imaging systems 121 and electro-stimulation device 170 in the system 100, the electro-stimulation device 170 and imaging systems 121 are not necessarily in one system or apparatus and do not need to work simultaneously. Additionally, images can be captured by the imaging systems 121 before generating the electric field with the electro-stimulation device 170.

As illustrated in FIG. 1A, a computer system 150 is provided to control the one or more imaging systems 121, to collect image data from the one or more imaging systems 121 before or at the time of electrical stimulation and to control the electro-stimulation device 170. In an embodiment, the computer system 150 includes a precision dosing process 140 to perform one or more steps of a method described below with reference to FIG. 2B. In another embodiment, the control system 150 includes a treatment outcome improvement mode process (e.g. cognitive improvement model process 141) to perform one or more steps of a method described below with reference to FIG. 2A. In various embodiments, the computer system 150 comprises one or more general purpose computer systems or upgraded computer systems that include graphics processing units, as depicted in FIG. 13 or one or more chip sets as depicted in FIG. 14, and instructions to cause the computer or chip set to perform one or more steps of a method described below with reference to FIGS. 2A and 2B.

Figures 1B, 1C:
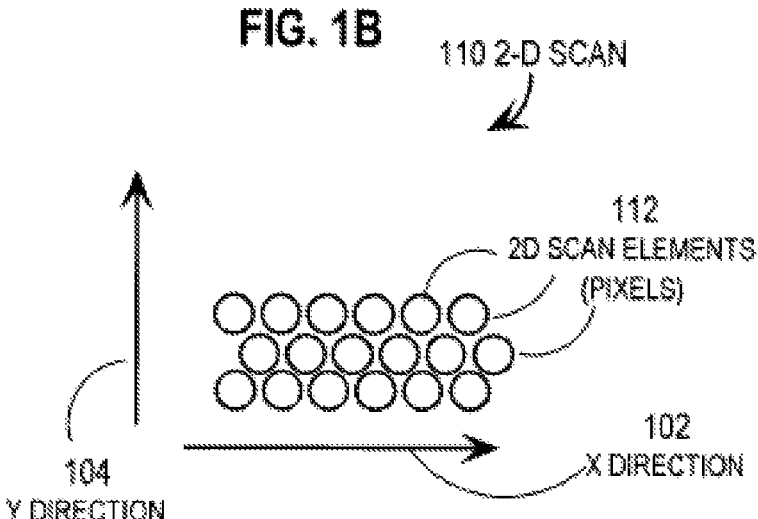
FIG. 1B is a block diagram that illustrates example scan elements in a 2D scan, such as one scanned image from a MRI or CT scanner.
FIG. 1C is a block diagram that illustrates a plurality of example voxels within a fixed frame of reference of the electro-stimulation device of FIG. 1A.

FIG. 1B is a block diagram that illustrates scan elements in a 2D scan 110, such as one scanned image slice of the volume 124 from the imaging system 121, such as a CT scanner. The two dimensions of the scan 110 are represented by the x direction arrow 102 and the y direction arrow 104. The scan 110 consists of a two dimensional array of 2D scan elements (pixels) 112 each with an associated position. Typically, a 2D scan element position is given by a row number in the x direction and a column number in the y direction of a rectangular array of scan elements. A value at each scan element position represents a measured or computed image intensity that represents a physical property (e.g., X-ray attenuation, or resonance frequency of an MRI scanner) at a corresponding position in at least a portion of the spatial arrangement of the living body. The measured property is called image intensity hereinafter and is treated as a scalar quantity. In some embodiments, two or more properties are measured together at a pixel location and multiple image intensities are obtained that can be collected into a vector quantity, such as spectral intensities in MRSI. Although a particular number and arrangement of equal sized circular scan elements 112 are shown for purposes of illustration, in other embodiments, more elements in the same or different arrangement with the same or different sizes and shapes (e.g. equal sized square scan elements) are included in a 2D scan.

FIG. 1C is a block diagram that illustrates the plurality of voxels 122 that are defined in the volume 124 within a fixed frame of reference of the electro-stimulation device 170 of FIG. 1A. The fixed frame of reference of the electro-stimulation device 170 is defined based on the x-direction 102, y-direction 104 and z-direction 106. Thus, in an example embodiment, a particular voxel 122 within the volume 124 in the frame of reference of the electro-stimulation device 170 is assigned a unique x-value, y-value and z-value. Although a particular number and arrangement of equal voxel 122 are shown for purposes of illustration, in other embodiments, more voxels 122 in the same or different arrangement with the same or different sizes and shapes (e.g. equal sized cube elements) are included in the frame of reference of the radiation source 170. In an example embodiment, the voxel 122 has a length in a range of 0.5-3 millimeters, a width in a range of 0.5-3 millimeters and a depth in a range of 0.5-3 millimeters.

FIGS. 2A and 2B are flow diagrams that illustrates an example of methods 200, 250 for determining dose characteristics for electro-stimulation of the brain, for purposes of improving treatment outcome (e.g. cognitive function). Although the flow diagrams of FIGS. 2A and 2B are depicted as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

FIG. 2A is a block diagram that illustrates an example of a method 200 to determine parameter values of an electric field within a head of a subject to improve treatment outcome (e.g. to improve cognitive function), according to an embodiment. In an embodiment, in steps 202 and 204, the voxels 122 are defined and tissue measurements are obtained to indicate the tissue type of each voxel 122 within the subject 190. In step 202, the set of voxels 122 within the frame of reference of the electro-stimulation device 170 are determined. In step 204, tissue measurements are obtained that indicate the tissue type of each voxel 122 in the set of voxels in the head 192 of the subject 190. In an example embodiments, steps 202 and 204 are performed using individual T1-weighted images that were converted from DICOM to NIfTI using dcm2niix [48] and resampled with the FreeSurfer v6.0.0 image analysis suite (http://surfer.nmr.mgh.harvard.edu/) into a 256 mm3 field of view (RAS orientation), 1 mm$^3$ voxel size. In an example embodiment, the computational models of current density were computed using the Realistic vOlumetric-Approach to Simulate Transcranial Electric Stimulation (ROAST; https://www.parralab.org/roast/) toolbox [35] with parallel processing on a high performance cluster with 50 CPU cores and 175 GB of RAM provided by the Research Computing at the University of Florida (HiPerGator). In an example embodiment, the resampled T1 images (256×256×256, 1 mm$^3$) were individually processed in parallel using ROAST. In one embodiment, the segmentation process was carried out in FreeSurfer to classify tissue types into gray and white matter. FreeSurfer segmentations were visually inspected and manually corrected for errors before reprocessing through FreeSurfer—a procedure that has been validated against manual segmentation [51] and histological measures [52]. Segmentations from FreeSurfer were then combined with segmented CSF, bone, skin, and air from ROAST. In one embodiment, segmentation quality was visually inspected by overlaying segmented masks onto their respective T1-weighted images.

In an embodiment, in step 206 an outcome measure or treatment outcome (e.g., cognitive function) of the subject 190 is assessed. FIG. 3 is an image that illustrates an example of a test 300 to assess a cognitive function of a subject, according to an embodiment. In an embodiment, the test 300 of FIG. 3 is performed by outputting the images on a display (e.g. display 1314 of the computer system of FIG. 13) and the subject subsequently provides input with an input device (e.g. input device 1312 of the computer system of FIG. 13). In one embodiment, in step 206 the subject's 190 working memory is assessed with an in-scanner N-back task only given at baseline and post-intervention. The task paradigm for each run consisted of four blocks of two-back and four blocks of zero-back presented in a randomized order with 20-seconds of rest between blocks. During the two-back, participants viewed uppercase letters, one at a time. A screen with a central crosshair (+) was presented during the inter-trial interval. The stimuli appeared for 1-second, followed by a crosshair for 3-second, providing a 4-second window to make a response. Details of the N-back task procedure are outlined in the prior paper [49]. Participants performed practice on the N-back task (two- and zero-back) outside of the scanner to ensure understanding of the task at both baseline and post-intervention visits. Two-back performance change (i.e., pre-/post-intervention) was analyzed as a composite percent improvement score for accuracy and reaction time (ΔAccuracy+ΔRT/2).

In an embodiment, in step 208 an electric field is generated by the electro-stimulation device 170 at each voxel 122 inside the head 192 of the subject 190. In an embodiment, step 208 is performed based on one or more parameters (e.g. number of electrodes 192, placement position of the electrodes 192, current intensity of the electrodes 192, etc.) of the electro-stimulation device 170. FIG. 4A is an image that illustrates an example of the electro-stimulation device 170 including electrode pads 402a, 402b of the electro-stimulation device of FIG. 1A positioned on a head 192 of the subject 190, according to an embodiment. FIG. 4B is an image that illustrates an example of electrodes 404a, 404b of the electro-stimulation device 170 of FIG. 1A positioned on the head 192 of the subject 190, according to an embodiment.

In an embodiment, in step 208 the electro-stimulation device 170 is a device configured to perform EBS. In an example embodiment, the electro-stimulation device 170 is 1×1 tDCS (Soterix Medical, tDCS-CT for clinical trials) applied using two 5×7 cm2 pad electrodes 402a, 402b soaked in 0.9% NaCl (4 ml per side, 8 ml total per sponge) at F3 (cathode) and F4 (anode) location. In another example embodiment, the locations of the electrodes 193 were determined with head measurements using the International 10-20 system to locate F3-F4 locations at each session. In an example embodiment, subjects were stimulated at 2 mA intensity for 20-minutes with a 30-second current ramp up and down, with a total of 10 stimulation sessions over 14-days. In an example embodiment, each session included 40-minutes computerized cognitive training for working memory with stimulation delivered during the first 20-minutes. In an embodiment, details of the computerized training tasks are described in [49]. No significant effects of unblinding or differences in sensation were found for active vs. sham participants in the parent study [47]. In an example embodiment, the electrodes 404a, 404b (5×7 cm$^2$) were constructed from 3D captured electrode models as reported in [26] and added to the segmented models in ROAST. In an example embodiment, default conductivity values of 5.9× 107 S/m and 0.3 S/m were assigned to the electrode and gel layers, respectively [55]. In one embodiment, a +2 mA voltage boundary condition was assigned to the anode electrode at the F4 location, while a −2 mA voltage boundary condition was assigned to the cathode electrode at the F3 location (FIGS. 4A-4B). Although the example embodiments above discussed specific values for various parameters of the EBS (e.g. current intensity value, number of stimulation sessions, period time over which the sessions were conducted, conductivity values of the electrode and gel layers, etc.) these parameter values are not limiting and in other example embodiments, one or more of these parameter values can be adjusted or varied.

In an embodiment, in step 210 a value of one or more parameters of the electric field generated in step 208 in the head of the subject is determined. In one embodiment, the parameters of the electric field include one or more of a current intensity of the electric field and/or a direction of the electric field at each voxel 122. FIGS. 8A through 8C are images 800, 830, 860 that illustrate multiple parameter values of the electric field generated in the head of a subject, according to an embodiment. In an embodiment, the images 800, 830, 860 depict a magnitude of the current intensity of the electric field at each voxel 122 based on the color coded scale 802. In another embodiment, the images 800, 830, 860 depict a direction (e.g. vectors of the electric field) of the electric field at each voxel 122. In an embodiment, the image 800 represents the Coronal (xz) plane, the image 830 represents the Sagittal (yz) plane and the image 860 represents the Axial (xy) plane.

In one embodiment, in step 210 an amplitude of the current density is determined based on electrical properties of the tissue type at each voxel 122. In an example embodiment, in step 210 isotropic conductivity values were assigned to each voxel 122 based on the tissue type measurement of each voxel 122 (from step 204) [49]. In one example embodiment, table 1 below provides isotropic conductivity values used for various tissue types. In another example embodiment, table 2 provides characteristic values of the isotropic conductivity for various tissue types, such as minimum values (min), maximum values (max), mean values (mean), weighted mean values (wt. mean) and standard deviation values (sd) used for various tissue types. Although Table 1 provides example isotropic conductivity values of various tissue types and Table 2 provides example characteristic values of the isotropic conductivity for various tissue types, the embodiments of the present invention are not limited to these values in Tables 1 and 2.

TABLE 1

The tissue conductivity values for six tissue types.

| Tissue types | σ (S/m) | Reference |
|---|---|---|
| White matter | $1.26 \times 10^{-1}$ | Huang et al. [52] |
| Gray matter | $2.76 \times 10^{-1}$ | Huang et al. [52] |
| Cerebrospinal fluid (CSF) | 1.65 | Huang et al. [52] |
| Skin | $4.65 \times 10^{-1}$ | Huang et al. [52] |
| Bone | $1.0 \times 10^{-1}$ | Huang et al. [52] |
| Air | $2.5 \times 10^{-1}$ | Huang et al. [52] |

TABLE 2

Minimum, Maximum and Mean tissue conductivity values
for typical tissue types measured in low frequency.

| Tissue Types | Min (S/m) | Max (S/m) | Mean (S/m) | Wt. Mean (S/m) | SD (S/m) | Source |
|---|---|---|---|---|---|---|
| Whole brain | 0.054 | 13.75 | 1.059 | 0.3746 | 0.1322 | [83] |
| GM | 0.06 | 2.47 | 0.5981 | 0.466 | 0.2392 | [83] |
| WM | 0.0646 | 0.81 | 0.24 | 0.2167 | 0.1703 | [83] |
| WM_perp | 0.062 | 0.439 | 0.1216 | 0.1175 | 0.0495 | [83] |
| WM_par | 0.0543 | 0.915 | 0.1352 | 0.1226 | 0.0929 | [83] |
| CSF | 1 | 2.51 | 1.6922 | 1.71 | 0.2981 | [83] |
| Whole skull | 0.0182 | 1.718 | 0.0708 | 0.016 | 0.019 | [83] |
| Spongy | 0.0012 | 0.289 | 0.0559 | 0.0497 | 0.0735 | [83] |
| Compact (outer, inner) | 0.0008 | 0.0129 | 0.0045 | 0.0046 | 0.0016 | [83] |
| Scalp | 0.137 | 2.1 | 0.5345 | 0.4137 | 0.176 | [83] |
| Fat | 0.25 | 0.6 | 0.425 | 0.425 | 0.247 | [83.84] |
| Muscle | 0.1482 | 0.4167 | 0.3243 | 0.3243 | 0.1526 | [1] |
| Blood | 0.433 | 0.7622 | 0.5799 | 0.5737 | 0.106 | [1] |

For purposes of Table 2, GM denotes gray matter; WM denotes white matter; and CSF denotes cerebrospinal fluid.

In one embodiment, volumetric meshes of each tissue type were generated using iso2mesh [53]. Boundary conditions were assigned within ROAST and a finite element solver, getDP [54], was used to compute voltage solutions to the Laplace equation, $-\nabla \cdot (\sigma \nabla V)=0$, in the meshed models, where V is the electric potential within the volume and σ is the tissue conductivity. In yet another example embodiment, additional MATLAB routines to compute current density (J) from electric field (E) and tissue conductivity (σ) were added in accordance with Ohm's law: $J=\sigma E$. Current density (J) is a useful metric for determining the dosage of current ($A/m^2$) induced in the brain from electrical stimulation. Current density also represents a unit of current directly adjustable through alteration of applied stimulation intensity (e.g., 2 mA vs. 2.3 mA) for the purposes of individualized dosing calculations. The intensity of current at each voxel was calculated with the function:

$$\|\vec{J}\| = \sqrt{J_x^2 + J_y^2 + J_z^2} \qquad (1)$$

In another embodiment, the direction of current density in each coordinate plane was separated from intensity by deriving the zenith angle, θ between $\vec{J}$ and the z-axis, and the azimuthal angle, φ between the projection of $\vec{J}$ onto the xy-plane, $\vec{J}'$ and the x-axis:

$$\theta = \cos^{-1} \frac{J_z}{\sqrt{J_x^2 + J_y^2 + J_z^2}} \qquad (2)$$

$$\varphi = \tan^{-1} \frac{J_y}{J_x} \qquad (3)$$

In an example embodiment, current density values were computed in native space and masked using individual participants' white and gray matter voxels to restrict current values within brain region only and reduce the number of features submitted into the classifier. Masked values were then transformed with the UFAB-587 tissue probability map [28] into MNI space using SPM's normalise function [56]. Median values of J before and after the transformation were computed as a quality check for transformation errors (r=0.998).

In one embodiment, in step 208, pad electrodes (5×7 $cm^2$), placed according to the standard 10-10 EEG system [85, 86], were simulated as anodes in 71 locations with a fixed, "reference" cathode at $I_z$ (i.e., two electrodes per model). Model solutions generated in all electrode locations provided 71 unique electric field distributions to serve as the lead field for each head model. Thus, in step 210 the net electric field for any electrode pair was computed through linear combination of the lead field yielded by each bipolar configuration [87-90]. Generated electric fields (EF, [$Vm^{-1}$]) were converted into current densities (J [$Am^{-2}$]), using equations 1-3.

In an embodiment, in step 212 the test of step 206 to assess the cognitive function of the subject 190 is repeated. In other embodiments, in steps 206 and 212 other metrics are measured and compared to assess treatment outcome other than cognitive function (e.g. physical function, mental health function, neuroimaging, etc.)

In an embodiment, steps 204 through 212 are repeated for a plurality of subjects 190. In one embodiment, steps 204 through 212 are repeated for a plurality (e.g. fourteen) of healthy older adults. In an example embodiment, the plurality of subjects received 20 min of 2 mA EBS (e.g. tDCS) stimulation (F3/F4) in step 208. In another example embodiment, steps 204 through 212 are repeated a number (e.g. ten) of times for each subject over a duration (e.g. during a two-week cognitive training intervention). In an example embodiment, the cognitive function of each subject is assessed at steps 206 and 212 (e.g. before and after step 208). In an example embodiment, fourteen healthy older adults receiving active-tDCS stimulation were selected for further analysis by the current study [mean (sd) age=73.57 (7.84), mean MoCA=27.85 (1.79), 7F:7M]. In one embodiment, a T1-weighted dataset of these fourteen subjects was utilized to create individualized FEM. Details of the clinical trial dataset (NCT02137122) has been previously reported [91, 92]. In an embodiment, in steps 210, the electrical current density distribution in each brain was computed using an open-source FEM software ROAST v3.0 [41]. In this embodiment, in step 204, individual head volumes were segmented into 6 tissue types. Ventricular CSF, white, and gray matter were segmented using Freesurfer v6.0.0 (http://surfer.nmr.mgh.harvard.edu/). Meningeal CSF, bone, skin, and intracranial air were segmented in ROAST [93]. Individual tissue types were assigned conductivity values. In an example embodiment, all subjects were screened for eligibility based on study inclusion criteria detailed in [47]. Informed written consent was obtained from subjects prior to study procedures.

In an embodiment, in step 214 the plurality of subjects who performed steps 204 through 212 are classified into two or more groups. In one embodiment, the plurality of subjects who performed steps 204 through 212 are classified into groups based on a change in the assessed cognitive function from step 206 to step 212. In one example embodiment, in step 214 the plurality of subjects are separated into a first group of subjects (e.g. change in the cognitive function from step 206 to step 212 is greater than a threshold, such as a median for the plurality of subjects) and a second group of subjects (e.g. change in the cognitive function from step 206 to 212 is less than the threshold, such as the median for the plurality of subjects). In one embodiment, the first group of subjects are "responders" while the second group of subjects are "non-responders".

In an example embodiment, in step 214 subject classes were determined by separating subjects into binary groups based on pre/post-intervention performance changes on the two-back working memory task above or below the median. In an example embodiment, the first group of subjects is the EBS (e.g. tDCS) responder class (n=7) with an average performance increase of 22% (from step 206 to step 212) whereas, the second group of subjects is an EBS (e.g. tDCS) non-responder class (n=7) that was found to have an average 9% increase in two-back performance (F(1)=21.02, p<0.001).

In an embodiment, when performing steps 206 through 212 for each subject, structural imaging and behavioral data were sourced from a phase-II pilot clinical trial that employed a randomized, triple-blinded (assessor, interventionist, participant) design (NCT02137122). This approach enabled examination of the combined effects of EBS (e.g. tDCS) with cognitive training on working memory function in healthy older adults [49].

In an embodiment, in step 216 one or more parameter values of the electric field from step 210 for the first group of subjects are compared with the one or more parameter values of the electric field for the second group of subjects, in order to determine those parameter values of the electric field which distinguish the first group of subjects from the second group of subjects. The inventors of the present invention recognized that many parameter values of the electric field from step 210 do not considerably vary between the first group and second group of subjects, whereas other parameter values of the electric field do considerably vary between the first group and second group of subjects. The inventors of the present invention recognized that if those parameter values of the electric field that distinguish the first group of subjects from the second group of subjects were determined, they could be used to efficiently predict whether a new subject will experience cognitive function improvement based on parameter values of the electric field in the new subject.

In an embodiment, in step 216 a value of one or more parameter values of the electric field are determined (based on the parameter values of the electric field from step 210) which distinguish the first group of subjects from the second group of subjects. In an embodiment, in step 216 current models were passed through an SVM algorithm to characterize crucial EBS (e.g. tDCS) current components (e.g. intensity and direction) that induced working memory improvements in EBS (e.g. tDCS) responders (first group) versus non-responders (second group). In one embodiment, the SVM algorithm classified responders and non-responders based on the computed current density distribution per individual (see Albizu et al. 2020 for details [92]). In an embodiment, due to the high dimensionality of MRI data, feature selection was performed on the training data to further reduce the number of trained features. One popular method of feature selection is to filter the features via voxel wise t-tests between classes to select current elements with a significant group-level difference (p<0.01) as features for the subsequent prediction step [42,57,58]. The separating hyperplane with the maximal margin between the two classes of data was generated with an L2-loss SVM algorithm from LIBSVM[41]:

$$\min_{w,b} \frac{1}{2} w^T w + C \sum_{i=1}^{l} \max\left(1 - y_i\left(w^T x_i + b\right), 0\right)^2 \tag{4}$$

where $C \geq 0$ is a penalty parameter on the training error, $y_i$ and $x_i$ are the ground truth label and feature vector of the $i^{th}$ observation, respectively; and 1 is the number of observations in the dataset. w and b represent the weight and bias terms to be optimized. A linear kernel K was generated with the function:

$$K(x_i, x_j) = x_i^T x_j \tag{5}$$

Model performance was evaluated across ten iterations of leave-two-out cross-validation with stratified randomization between classes. Five folds of hyperparameter tuning of the penalty parameter C were performed on the training data. Following training, predictions of held out test data x were performed with the decision function:

$$f(x) = \mathrm{sgn}(w^T x + b) \tag{6}$$

Figures 11A, 11B, 11C, 11D, 11E, 11F:
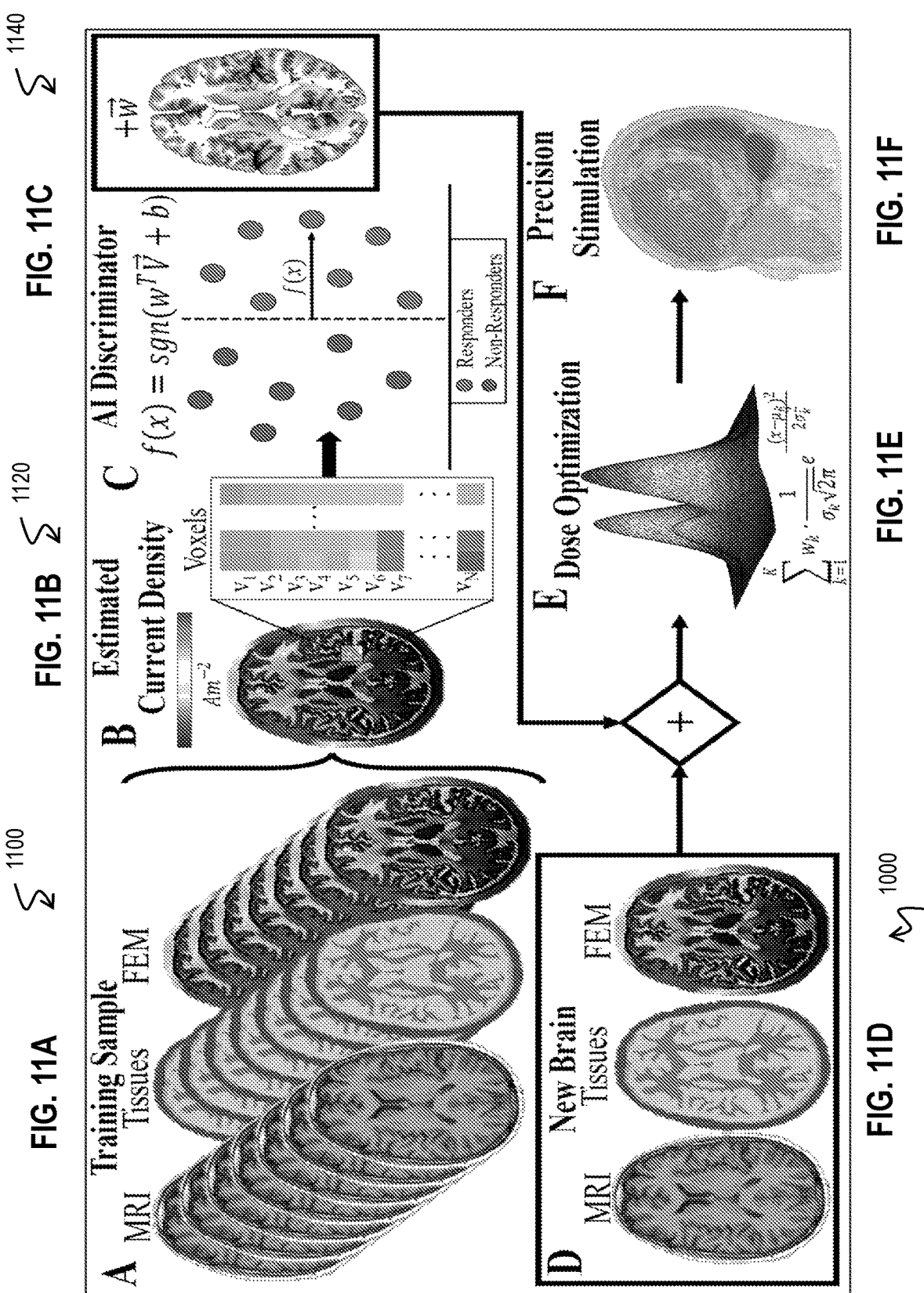

FIGS. 11A through 11C are images that depict various steps of the method of FIG. 2A, according to an embodiment. In one embodiment, these images show a schematic diagram of the proposed AI-defined tDCS precision dosing pipeline. FIG. 11A depicts one embodiment of a data set gathered in step 204, 208 and 210 for each subject in a group (e.g. 10 subjects). In this embodiment, FIG. 11A shows an independent dataset of MRI-images that are used to train the AI discriminator. Additionally, FIG. 11A depicts images that indicate the tissue measurements obtained in step 204 for each subject. FIG. 11A also shows images (FEM) that indicate the current density of the electric field obtained in step 210 for each subject.

FIG. 11B illustrates an image that shows the value of the current density of the electric field obtained in step 210 for each subject, where the value of the current density is based on the color coded scale. Specifically, individual computational model (Am$^{-2}$) with colors representing estimated current density within each voxel of the head are used as features.

FIG. 11C illustrates an example of a graph generated when performing steps 214 and 216. In this embodiment, these data are submitted to an AI discriminator to predict treatment response (e.g. using equation 3) to output feature weights representing the predictive power of each voxel. In this embodiment, FIG. 11C depicts an image of the brain that indicates the values determined in step 216 (e.g., the weight w values of the electrical current density at each respective voxel) based on the responder group.

In an embodiment, the SVM algorithm is used to determine one or more parameter values of the electric field to distinguish the first group of subjects from the second group of subjects. In one embodiment, the parameter values determined by the SVM are assessed using a receiver operating characteristic (ROC) curve which depicts the true positive rate (e.g. rate at which the one or more parameter values correctly predicted whether a subject is in the first group of subjects) and a false positive rate (e.g. rate at which the one or more parameter values falsely predicted that a subject is in the first group of subjects). As appreciated by one skilled in the art, the area under the ROC curve (AUROC) is a measure of how often the parameter value correctly predicted a result. An AUROC of 1 means that the parameter value corrected predicted a result 100% of the time, an AUROC of 0 means that the parameter values correctly predicted a result 0% of the time and an AUROC of 0.5 indicates that the parameter value correctly predicted a result 50% of the time (e.g. equal to a chance or coin flip prediction).

FIG. 5B is an image that illustrates an example of ROC curves 550 to predict an outcome of the cognitive test of FIG. 3 for multiple subjects based on different parameters of the electric field, according to an embodiment. In an embodiment, the horizontal axis 552 is specificity or false positive rate and the vertical axis 554 is sensitivity or true positive rate. FIG. 5A is an image that illustrates an example of a histogram 500 depicting the area under the receiver operating curves (ROC) 550 of FIG. 5B for different parameters of the electric field to predict an outcome of the cognitive test of FIG. 3, according to an embodiment. In an embodiment, the horizontal axis 502 identifies one or more parameters of the electric field and the vertical axis 504 is the AUROC for the respective curves in FIG. 5B for the different electric field parameters. In an embodiment, the histogram 500 depicts a bar 510 that represents the area under the ROC curve 556 (FIG. 5A) for the parameter of current intensity of the electric field. The bar 510 indicates that the AUROC for the current intensity parameter is about 0.806 and thus the current intensity parameter of the electric field has about an 81% accuracy. In an embodiment, the histogram 500 depicts a bar 508 that represents the area under the ROC curve 558 (FIG. 5A) for the parameter of direction of the electric field. The bar 508 indicates that the AUROC for the direction parameter is about 0.776 and thus the direction parameter of the electric field has about a 78% accuracy in predicting whether a subject is within the first group or second group of subjects. In an embodiment, the histogram 500 depicts a bar 506 that represents the area under the ROC curve 555 (FIG. 5A) for the combined parameters of current intensity and direction of the electric field. The bar 506 indicates that the AUROC for the combined current intensity and direction parameters is about 0.749 and thus the combined current intensity and direction parameters of the electric field has about a 75% accuracy in predicting whether a subject is within the first group or second group of subjects.

In an embodiment, computational models of current intensity, current direction, and their interaction, all demonstrated above chance performance for predicting treatment response (i.e., AUROC>50%). The AUROC revealed that the probability of current intensity will rank a randomly chosen responders (subject from the first group) higher than a randomly chosen non-responders (subject from the second group) was 81% [69]. Classification of the direction alone and combined models of direction and intensity produced AUROCs of 78% and 75%, respectively. Computational models of current intensity alone marginally outperformed current direction and the combination of current direction with intensity in the classification problem (FIG. 5B). However, a one-way ANOVA between the AUC of each current characteristic (F(2)=1.31, p=0.288) revealed a non-significant difference between the three variables. The support vector machine classification of all three models correctly differentiated tDCS responders from non-responders with averaged overall accuracy of about 86.43%. The 95% confidence interval of classification accuracy for these models was between [CI: 85.03-87.83%].

In one embodiment, in step 216 SPSS Statistics 25 (https://www.ibm.com/analytics/spss-statistics-software) and the Statistics and Machine Learning toolbox in MAT-LAB 2019b [65] were used to carry out statistical analyses. One-way ANOVA was used to assess mean difference in model performance between the three data types (direction, intensity, direction x intensity). A secondary set of analyses was aimed at determining the characteristics of current with the voxels determined to be essential for treatment response. Within these regions, Pearson's correlation analyses were used to assess the relationship of behavioral response with field characteristics. Linear regression analyses were used to fit lines of least square residuals. Hedge's g was computed to define effect sizes of mean differences, corrected for small sample bias [66]. Since all fourteen participants in our study were individuals with no familial relationship and each participant's data were collected under the same condition, these data points met the statistical assumptions of independently and identically distributed (iid) data. To determine the normality of each variable, we tested the null hypothesis that each data vector comes from a standard normal distribution, against the alternative that it does not come from such a distribution, using the one-sample Kolmogorov-Smirnov test [67,68]. The null hypothesis of a normal distribution was not rejected by the Kolmogorov-Smirnov test for all variables analyzed.

In an embodiment, in step 216 one or more discrimination maps are generated that indicate a contribution (e.g. in percentage) that each voxel contributes to the classification of the first group of subjects (responders) from the second group of subjects (non-responders). FIG. 6 is an image 600 that illustrates an example of multiple discrimination maps that indicate a contribution of each voxel to distinguish groups of subjects based on an outcome of the cognitive test of FIG. 3, according to an embodiment. In an embodiment, a scale 602 is provided in FIG. 6 which includes a color-code indication of the relative contribution (e.g. with a percentage value) of each voxel to the classification of the first group (responders) from the second group (non-responders).

In another embodiment, in step 216 one or more graphs are presented that illustrate the distinction between the first group (responders) and second group (non-responders) in terms of the parameter values (e.g. current intensity) distributed over the voxels 122. FIGS. 7A through 7D are graphs 700, 730, 750, 770 that illustrate parameter values of the electric field generated in the head of multiple subjects to predict outcomes of the multiple subjects performing the cognitive test of FIG. 3, according to an embodiment. In an embodiment, the horizontal axis 702 is current intensity (in units of mA); the vertical axis 704 is a percentage of voxels 122 (e.g. with a current intensity value along the axis 702); the vertical axis 706 is a cumulative percentage of voxels 122 (e.g. with a current intensity less than or equal to the value along the axis 702); the horizontal axis 752 is an average current intensity of the voxels 122; the vertical axis 754 is a behavioral change (based on steps 206 and 212); the horizontal axis 772 is used to distinguish responders from non-responders and the vertical axis 774 is a mean current intensity of the voxels 122 depending on the responders or non-responders along the axis 772.

17 | 18

Figures 7A, 7B, 7C, 7D:
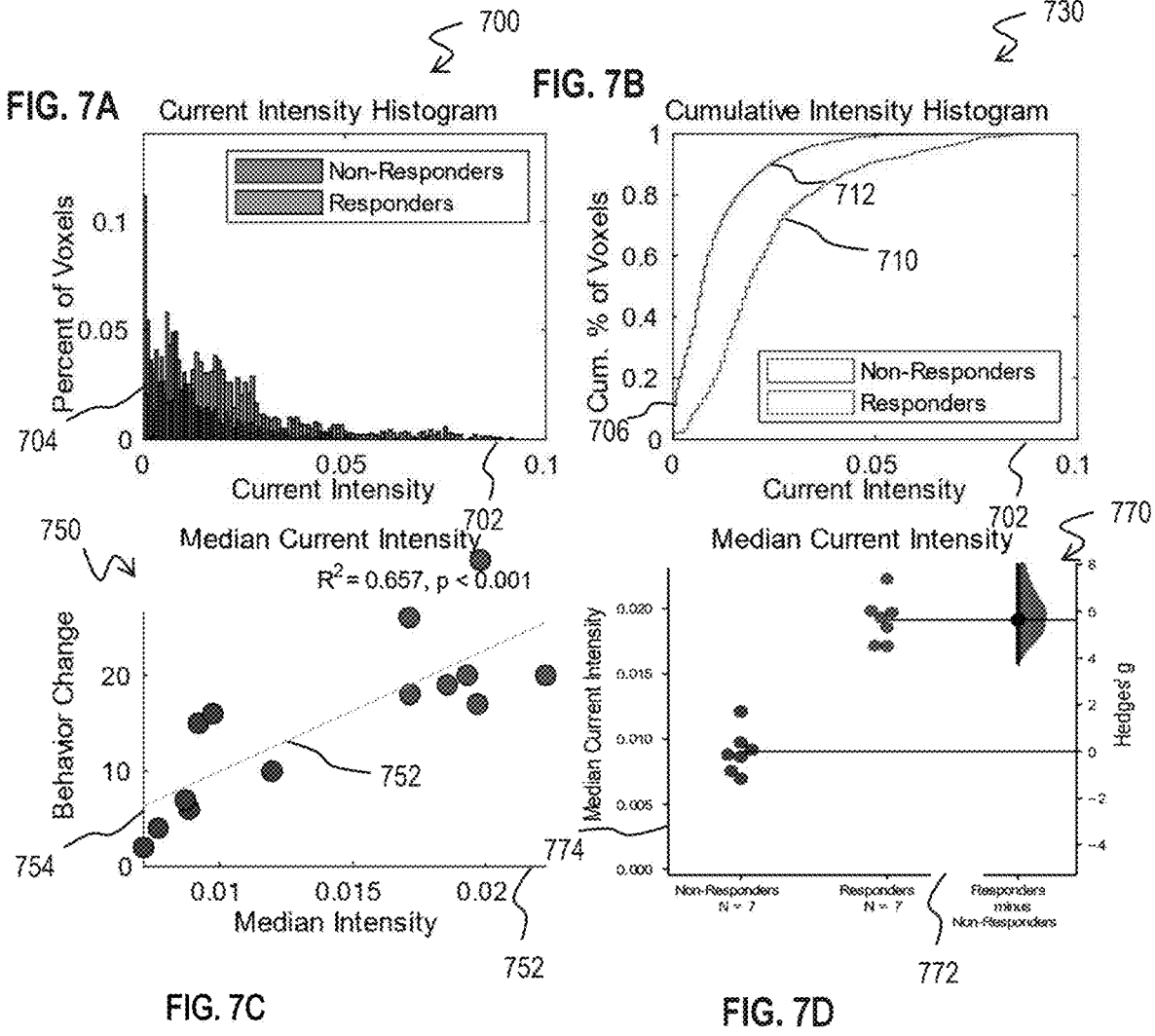

In one embodiment, in step 216 within the voxels predictive of EBS (e.g. tDCS) response (FIG. 6), responders (first group of subjects) were found to have greater current intensity within these regions (FIGS. 7A-7B), with greater median (r=0.811, p<0.001) and mean current intensity (r=0.720, p=0.004) correlated with treatment response (FIG. 7C). Responders produced an effect size of 5.63 (Hedges' g; FIG. 7D) with a 95% confidence interval between [CI: 3.82-7.94] and a significant two-sided permutation t-test (p<0.001, 5000 permutations). In one embodiment, behavior change was also related to the azimuthal angle, the angle of the current vector in the axial plane between the electrodes, $\varphi$(r=0.774,p=0.001) and the x-magnitude of the current vector, J_x (r=0.832, p<0.001). Behavior change was not related to zenith angle, $\theta$ (r=0.289, p=0.32; see Supplemental FIG. 3), y-magnitude of the current vector, $J_y$ (r=0.222, p=0.45), or the z-magnitude of the current vector, $J_z$ (r=0.281, p=0.33). Thus, current angled toward the cathode related to positive outcomes (see FIG. 8A-C for representative model). In an example embodiment, on average, the current direction computed within the xy-plane, $\varphi$, showed greater percentages of positive angles in responders, whereas non-responders demonstrated greater percentages of negative angles. Thus, in this example embodiment, an enhanced convergence of current direction toward the cathode was found within responders (FIG. 8D). In one embodiment, shifts in electrode location are inversely correlated to behavior change (anode: r=−0.732, p=0.003, cathode: r=−0.775, p=0.001), as well as changes in mean current intensity (anode: r=−0.523, p=0.06, cathode: r=−0.623, p=0.02) and azimuthal angle (anode: r=−0.579, p=0.03, cathode: r=−0.794, p<0.001) within these voxels.

In an embodiment, in step 216 For feature weight generation and deployment, a final model was trained on all fourteen current density maps to derive overall classification weights, w (i.e., the model parameters learned by the optimization function during the training phase, cf. Equation 4). The feature weights at each voxel, representing the relative contribution of each voxel to the classification, were separated by positive and negative weights that predict responders and non-responders, respectively [63]. Positive and negative weights were divided by their respective sum of weights to compute the percent contribution of each voxel toward either positive or negative prediction. To demonstrate specific brain regions that predict working memory improvements, regions of interest (ROIs) were defined using the Harvard-Oxford atlas [64] and ranked based on their average voxel percent contribution.

In one embodiment, different regions of the brain are categorized based on an average contribution (e.g. with a percentage value) of each voxel 122 towards the classification of the first group of subjects from the second group of subjects. FIG. 9A are images 900 that illustrate a mean contribution of different regions of the brain of the subject to distinguish groups of subjects based on an outcome of the cognitive test of FIG. 3, according to an embodiment. FIG. 9B is a histogram that depicts the contribution of different regions of the brain of the subject to distinguish groups of subjects based on an outcome of the cognitive test of FIG. 3, according to an embodiment. Table 3 below lists the different regions of the brain, ranked according to the relative contribution (e.g. using a mean value for the voxels 122 within the respective region) of each region to the classification of the first group of subjects from the second group of subjects in step 214.

TABLE 3

| Rank | ROI Label | Mean Contribution per Voxel (%) |
|---|---|---|
| 1 | R Superior Frontal Gyrus | 0.0262 |
| 2 | L Superior Frontal Gyrus | 0.0198 |
| 3 | R Middle Frontal Gyrus | 0.0196 |
| 4 | L Putamen | 0.0196 |
| 5 | R Frontal Pole | 0.0175 |
| 6 | R Precentral Gyrus | 0.0156 |
| 7 | L Frontal Pole | 0.0152 |
| 8 | R Pars Opercularis | 0.0152 |
| 9 | L Caudate | 0.0142 |
| 10 | R Anterior Supramarginal Gyrus | 0.0137 |

In one embodiment, FIG. 9A and Table 3 illustrate the top ten ranked regions of interest (ROIs) based on the mean percent contribution per voxel within each region. In an example embodiment, FIG. 9B depicts the distribution of percent contribution across Harvard-Oxford ROIs. The horizontal axis 922 is mean contribution per voxel (in percentage) and the vertical axis 924 is an identifier for the region (ROI). In an example embodiment, the top ten ROIs predicted working memory improvements and were largely located in the frontal region underneath and between the electrodes (FIG. 9A). These ROIs were labelled in the Harvard-Oxford atlas as the: 1) Right Superior Frontal Gyrus, 2) Left Superior Frontal Gyms, 3) Left Caudate, 4) Right Caudate, 5) Left Middle Frontal Gyrus, 6) Right Middle Frontal Gyrus, 7) Left Middle Temporal Gyrus, posterior division, 8) Left Heschl's Gyrus, 9) Right Postcentral Gyrus, 10) Right Supramarginal Gyrus, posterior division (Table 3).

In an embodiment, the top ten ROIs that predict working memory improvements included the dorsolateral prefrontal cortex (DLPFC), ventrolateral prefrontal cortex (VLPFC), basal ganglia, and cingulo-opercular network regions [72]. In one embodiment, the DLPFC and VLPFC are critically involved in monitoring, maintaining, and manipulating task-relevant information. These processes are vital for working memory function [73-75]. Recent studies have reported increased functional connectivity within these regions paired with improvements in working memory performance following applications of tDCS [49,76]. The basal ganglia also play an important role in learning and memory [77]. Specifically, the basal ganglia have been suggested to work conjunctively with the middle frontal gyms to select information to be stored in working memory [78]. In addition, increased functional connectivity of the cingulo-opercular network (also referred to as the ventral attention/salience network) is associated with better performance on measures of fluid cognition (e.g., executive function) in older adults [79]. The SVM identified critical current features in brain regions previously associated with working memory performance and age-related cognitive decline, serving as an additional proof of principle for this approach.

In one embodiment, in step 216 the generated SVM model was highly accurate at classifying treatment response in older adults, based only on the distributed patterns of electric current. Using these methods, precision EBS (e.g. tDCS) dosing tailored to each individual can be generated to efficiently deliver equivalent current intensity within cortical regions that are essential for producing improvements in working memory. With optimization, application of these presented methods could potentially be expanded to improve EBS (e.g. tDCS) efficiency in not only older adults but also various mental health [7,80,81] and brain-based pathologies [8,9].

In one embodiment, the limited number of data points in the current study may affect the generalizability of the model. Thus in our future work, we will use a larger and more heterogeneous tDCS clinical trial dataset [82] (NCT02851511) which is near completion. To maximize the use of available data points and avoid overfitting in this study, we used two-level nested cross-validation to increase the number independent test samples and used 10 permutations to assess the retest reliability of these models. Average accuracy and confidence intervals across these permutations were used to estimate model performance on novel datasets. For simplicity of interpretation, we used a binary SVM to distinguish discrete classes, responders and non-responders; however, it is also feasible to utilize machine-learning algorithms to make continuous predictions (i.e., magnitude of improvement) [5]. As a proof of concept study for predicting tDCS responders, features submitted to the classifier were limited to the computational FEM. Introducing additional neuroimaging modalities and clinical data into the model may further enhance performance and predictive value of machine-learning based approaches for understanding tDCS treatment response.

In an embodiment, the present study investigated the essential characteristics of tDCS current (i.e., current intensity, current direction, etc.) by using a machine learning algorithm to predict tDCS effects on measured behavioral outcomes. Overall, in an example embodiment, both current direction and intensity are demonstrated to be critical components of stimulation response. Consistent with an initial hypothesis, the electric field components produced predictions of tDCS response beyond chance (i.e., AUC>50%). While current intensity did marginally outperform other variables, this difference was not statistically significant. Contrary to our second hypothesis, all tested variables were comparable in predicting behavior change. Using a small clinical trial dataset, the machine-learning algorithm presented in this paper was able to classify tDCS responders and non-responders with 86% accuracy based on patterns of current characteristics.

In an embodiment, FEMs were generated for each stimulation session and averaged across 10 sessions (see FIG. 11). In one embodiment, in step 210 electrode displacement was computed as the 3D Euclidean distance between modeled electrodes and the ideal location of F3-F4, derived from ROAST [55].

In an embodiment, the weights produced by the SVM algorithm revealed the brain regions that contributed most to predictions of treatment response. Within these regions, median and mean current intensity were found to positively relate to behavioral response, suggesting greater current intensity may produce greater behavioral response. Since tDCS is typically applied at a fixed dose across individuals, individual differences in anatomy are likely to cause varying amounts of current intensity within these essential brain regions. For instance, those with greater degrees of brain atrophy would have a decreased level of current intensity within stimulated brain tissues and thus may experience reduced efficacy from fixed dose tDCS. It is important to note that while the data demonstrates an association between delivery of larger amounts of current intensity and better behavioral responses, this does not necessarily mean that "more is better" universally. In an example embodiment, Samani et al. previously reported that applied current intensity beyond 2 mA demonstrates nonlinear alterations in neuronal excitability [62]. Thus, within the range of current intensities inducible in the brains of older adults receiving fixed 2 mA dose, increased current intensity appears beneficial for treatment response. Intensities beyond this range require further research.

In an embodiment, electrode orientation and location during EBS (e.g. tDCS) can also dictate the shape and location of stimulation contact area, altering the pattern of current flow within the brain [22]. In an example embodiment, both anode and cathode displacement were found to negatively affect intensity and direction of current within the brain as well as behavioral response. Minor electrode shifts (i.e., ≥1 cm) have been previously demonstrated to dramatically alter the current intensity by up to 38% [21,71]. Therefore, monitoring and increasing electrode placement accuracy via 3D capture techniques [26] may improve individual treatment response.

Figures 10A, 10B, 10C, 10D:
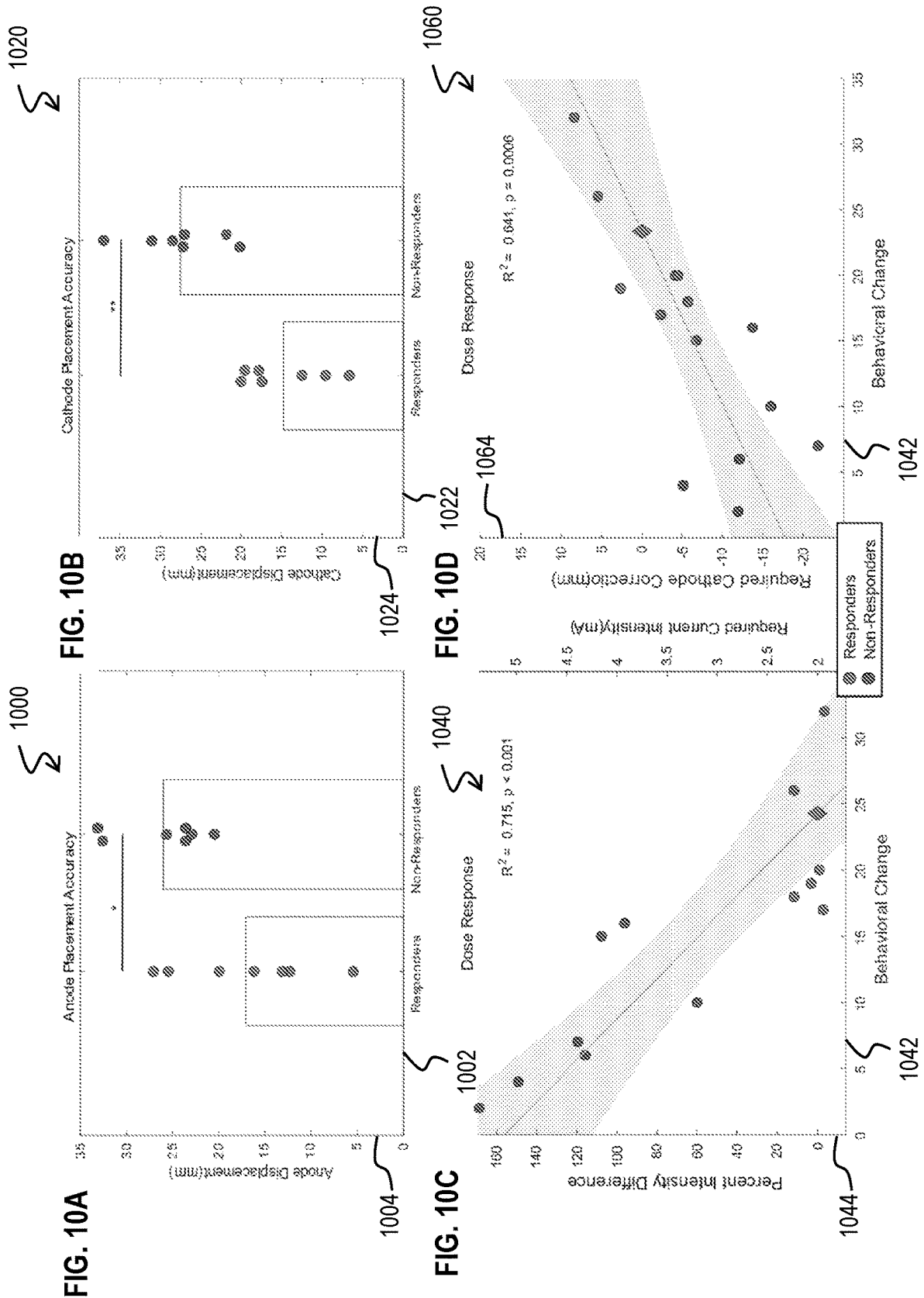

In an embodiment, in step 216 a location of the electrodes (e.g. 402a, 402b, 404a, 404b in FIGS. 4A-4B) are measured and compared with an ideal location (e.g. F3/F4 in the 10-20 system). In an example embodiment, in step 216 a displacement of each electrode is based on a difference between the measured location of the electrode and the ideal location. In another embodiment, in step 216 equation 6 is used to determine the optimal dosing parameters that are likely to convert non-responders (second group of subjects) into responders (first group of subjects). In an example embodiment, to match the mean profile of current characteristics demonstrated in responders, non-responders would require an average increase in applied current intensity of about 3.5 mA (e.g. or in a range from about 2.49 mA to about 4.16 mA and/or from about 1 mA to about 5 mA) and the cathode location should be shifted about 1.25 cm (e.g. or in a range from about 0.52 cm to about 2.22 cm) closer to the ideal 10-20 location. In an embodiments, FIGS. 10A and 10B demonstrate the relationship between differences in electrode placement and behavioral response. In an embodiment, the horizontal axis 1002 and 1022 are used to identify the responder/non-responder group. In another embodiment, the vertical axis 1004 indicates a cathode displacement in cm and the vertical axis 1024 indicates an anode displacement in cm. FIGS. 10C and 10D demonstrate the required shifts in intensity (10C) and electrode placement (10D) to match the mean profile of responders. In an embodiment, the horizontal axis 1042 and 1042 are used to identify a behavioral change (e.g. difference between steps 206 and 212). In another embodiment, the vertical axis 1044 indicates a required percentage change in the electric field intensity (in percentage) for the non-responders to become responders. Similarly, vertical axis 1064 indicates a required cathode displacement (in cm) for the non-responders to become responders.

In an embodiment, in step 218 the values of the one or more parameters of the electric field from step 216 that effectively distinguish the first group (responders) from the second group (non-responders) are stored in a memory of the computer system 150. In another embodiment, one or more parameters of the electro-stimulation device 170 (e.g. adjustment of the applied current, displacement of one or more of the electrodes relative to an ideal location, etc.) to convert a non-responder into a responder from step 216 are also stored in the memory of the computer system 150.

FIG. 2B is a block diagram that illustrates an example of a method 250 for determining parameter values of the electro-stimulation device 170 on a subject 190 to achieve improved cognitive function, according to an embodiment. Unlike the method 200 of FIG. 2A, which uses multiple subjects to determine one or more parameter values of the electric field at each voxel 122 that distinguishes responders from non-responders, in the method 250 of FIG. 2B the method determines one or more parameter values (e.g. current intensity, electrode placement, etc.) of the electro-stimulation device 170 for a new subject to improve a cognitive response of the new subject.

In an embodiment, steps 251 and 253 are similar to steps 201 and 203 of the method 200 with the exception that the steps are performed for a new subject.

In an embodiment, in step 255 the value of the parameters of the electric field from step 216 are obtained (e.g. retrieved from stored memory of the computer system 150).

In an embodiment, in step 257 a value of one or more parameters of the electro-stimulation device 170 are determined based on the parameter values of the electric field (from step 255) and the tissue measurements of the new subject (from step 253). In one embodiment, in step 257, steps 206 through 212 of the method 200 are performed on the new subject. In an embodiment, the values of the parameters of the electric field at each voxel 122 of the new subject are compared with the values of the parameters of the electric field from step 255. In an example embodiment, this comparison is used to assess whether the new subject is in the first group of subjects (responder) or the second group (non-responder) group of subjects. In other embodiments, step 206 and 212 are compared to assess whether the new subject is in the first or second group of subjects. In these embodiments, if the new subject is in the second group of subjects, step 257 includes one or more steps to adjust parameter values of the electro-stimulation device 170 to improve a cognitive response of the new subject (e.g. so the new subject is in the first group of subjects). In some embodiments, if the new subject is in the second group, then one or more parameter values of the electro-stimulation device 170 are adjusted based on step 216 (e.g. adjustment of the current intensity value, adjustment of the anode and/or cathode placement relative to ideal locations, such as F3/F4, etc.).

In some embodiments, where step 257 involves adjusting the current intensity of the device 170, to quantify the required input current for converting non-responders into the responder range, the formula:

$$\hat{I} = I_o\left(1 + \frac{J - x}{x}\right) \tag{7}$$

is employed, where x represents a non-responder mean current value (e.g. mean current value based on step 210 performed with the new subject), $J^-$ represents the target current values (i.e., average values computed in the responder group, obtained in steps 216 and 255), $I_o$ represents the original injected current (e.g., intensity of the current in performing step 208 with the new subject, such as 2 mA), and $$\frac{J - x}{x}$$

represents the percent difference. The optimal electrode displacement is defined as the non-responder displacement minus the mean responder displacement.

In an embodiment, after determining the one or more parameter values of the electro-stimulation device 170 in step 257, the electro-stimulation device 170 is then configured in step 259 based on these parameter values. In an example embodiment, one or more input devices 1212 of the computer system 150 are used to input the current intensity value such that the computer system 150 transmits a signal to the electro-stimulation device 170 with that current intensity. In other embodiments, in step 259 the cathode or anode are displaced (e.g. relative to the ideal F3/F4 position).

In an embodiment, in step 261 the electric field is generated by the electro-stimulation device 170 (as configured in step 259) at each voxel 122 of the new subject. In an example embodiment, after step 261 the improved cognitive response of the new subject is confirmed by performing steps 206 and 212 before and after step 261 to verify that the new subject is now in the responder group.

FIGS. 11D through 11F are images that depict various steps of the method of FIG. 2B, according to an embodiment. In an embodiment, FIG. 11D depicts an embodiment of images (e.g. tissue type measurements) obtained during step 253 for a new subject. In this embodiment, similar computational models of current density can be computed from MRI-images from a novel, treatment naïve brain.

FIGS. 11D and 11E show one example of performing steps 257 and 259, where the configuration of the electro-stimulation device for the new subject is determined based on the data obtained in step 253 (e.g. FIG. 11D tissue type data at each voxel) and the data obtained in step 216 (e.g. FIG. 11C electric field parameters of the responder group). In one example embodiment, FIG. 11E depicts that computational models of treatment naïve brains can be submitted to a weighted Gaussian mixture model to optimize tDCS dosing parameters.

FIG. 11F shows one example of performing step 259 and 261, where the electro-stimulation device is configured and the electric field is generated based on the dose optimization from step 257 (FIG. 11E). In an example embodiment, the electrode montage and injected current intensity that maximize the likelihood of treatment response are used as precision doses.

In an embodiment, steps 214 and 216 of the method 200 are performed using a Gaussian mixture model (GMM) of key features. Additionally, the GMM can be used to show that non-responders (e.g. the first group of subjects in step 214) subsequently receive an optimized dose in the method 250 (e.g. step 261) that is proximate to the dose received by the responder group (e.g. the second group of subjects in step 214). This indicates that the method 250 will likely improve the response of the non-responders which can be confirmed by the non-responder group repeating steps 206 through 214 after receiving the optimized dose in the method 250. In this example embodiment, an improve response of the non-responder group can be confirmed by comparing steps 206 and 212 when the non-responder group repeats steps 206 through 214 after receiving the optimized dose.

In this embodiment, a weighted, Gaussian mixture model (GMM) of key features (i.e., SVM feature weights, cf. FIG. 11C) from responders' current distribution was built to account for inter-personal variation in responders. Mean, variance, and SVM feature weight was used to estimate each Gaussian model. The likelihood ($\ell$) of a new subject belonging to the responders' current distribution was calculated using:

$$\ell(x_k|w_k, \mu_k, \sigma_k) = \sum_{k=1}^{K} w_k \cdot \frac{1}{\sigma_k\sqrt{2\pi}} e^{-\frac{(x_k - \mu_k)^2}{2\sigma_k^2}}$$

$w_k$ is the SVM weight, $\mu_k$ is the mean estimation, and $\sigma_k$ is the standard deviation of the $k^{th}$ feature. The likelihood estimate was used as a fitness metric to optimize tDCS parameters (i.e., electrode placement and injected current intensity in steps 257 and 259; see FIG. 11E-11F). In an example embodiment, in step 259 electrode positions were optimized from 4,970 potential electrode pairs (71 locations from the 10-10 system). Injected current intensity was optimized between 0.1 through 4.0 mA in 0.1 mA increments for a total of 40 possible input current levels. Table 4 below depicts an example embodiment of values of the current density to convert the seven non-responders (S1-S7) at each of the anodes and cathodes of the electro-stimulation device (e.g. in steps 259 and 261). The overall tDCS optimization space included 198,800 potential tDCS doses per person. After the optimization process, current density volumes of optimized doses within the non-responder group were passed back through the original SVM model for re-classification as responders or non-responders.

TABLE 4

| Precision doses generated to convert seven tDCS non-responders into responders | | | |
|---|---|---|---|
| | Current Intensity | Anode | Cathode |
| S1 | 3.4 mA | F4 | F3 |
| S2 | 2.0 mA | F6 | F5 |
| S3 | 3.1 mA | F4 | F3 |
| S4 | 2.7 mA | F4 | F3 |
| S5 | 2.8 mA | F4 | F3 |
| S6 | 2.4 mA | F4 | F3 |
| S7 | 2.0 mA | F6 | F5 |

Figures 12A, 12B, 12C, 12D, 12E, 12F:
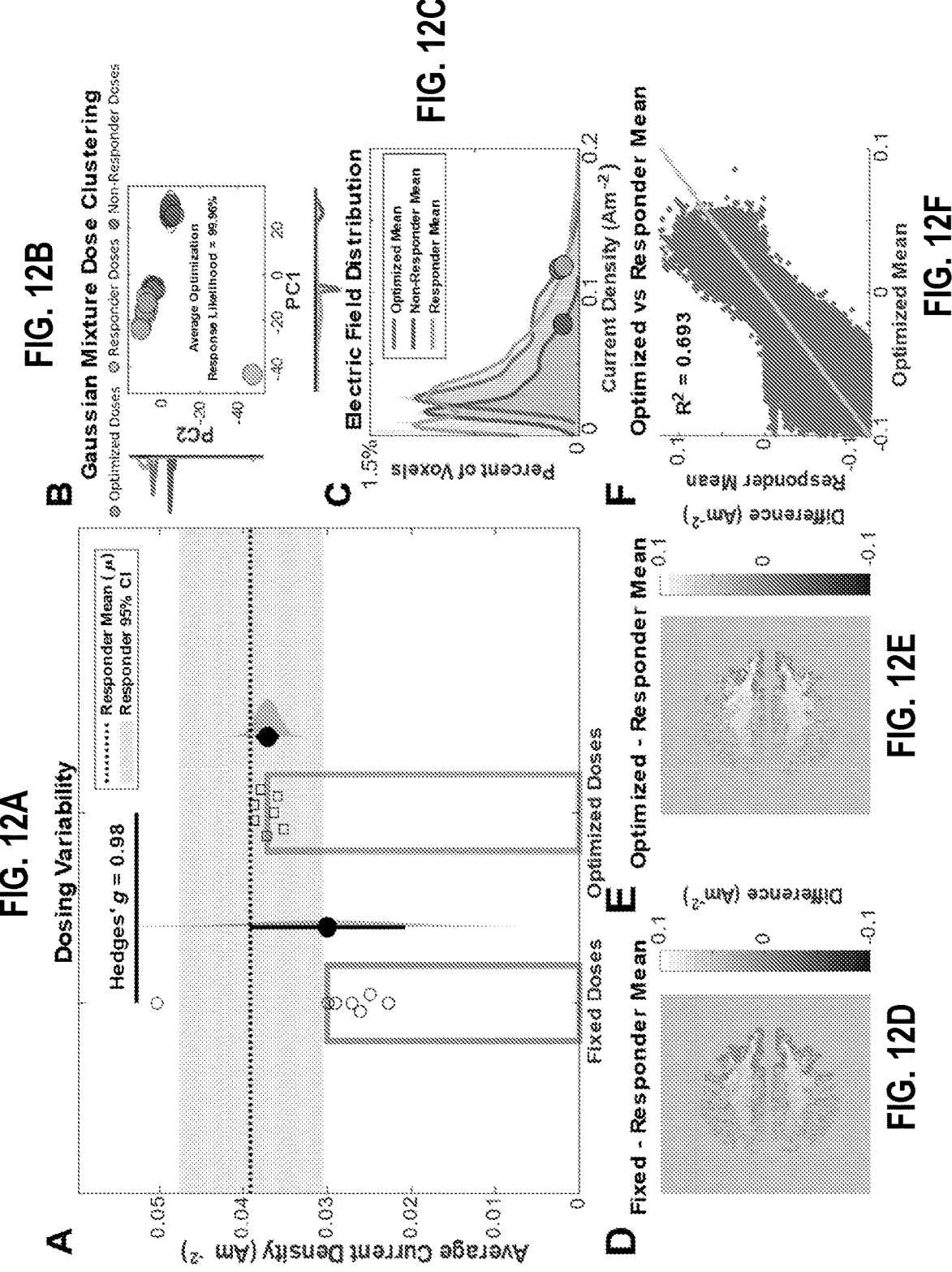

FIGS. 12A through 12F are images that depict a comparison between conventional fixed dosing and optimized dosing based on the methods of FIGS. 2A and 2B, according to an embodiment. FIG. 12A is similar to FIG. 7D. In an embodiment, FIG. 12A depicts the average current density for non-responder subjects based on steps 204 through 214. FIG. 12A also depicts the average current density of the same non-responder subjects after receiving the optimized dose (e.g. steps 253 through 261 of the method 250). Dosing variability and mean difference in average current density reaching the brain by fixed (red) versus optimized (blue). Black dots represent the mean. Error bars represent ±1 SD from the mean. Histograms represent the normal distribution of the sample.

FIG. 12B is a Gaussian mixture dose clustering of optimized (blue), tDCS responder (green), and tDCS non-responder (red). In this embodiment, the horizontal axis PC1 is a first principal component of the estimated current density and the vertical axis PC2 is a second principal component of the estimated current density. In an embodiment, FIG. 12B depicts that the values of the PC1 and PC2 components for the non-responder group (red) after steps 204 through 214 change to the optimized values (blue) based on performing the method 250. FIG. 12B shows that the optimized values (blue) of the PC1 and PC2 components of the non-responder group after the method 250 are proximate to the tDCS responder values (green) measured during steps 204 through 214. This indicates that the non-responder group should experience an improved cognitive response when steps 204 through 214 are repeated after the method 250. Histograms represent the smoothed distribution of the first and second principal component (i.e., PC1 and PC2) of estimated current density. A similar comparison is shown for the electric field distribution in FIG. 12C and how the optimized dose to the non-responder group results in an electric field distribution in the non-responder group after receiving the optimized dose that is proximate to the electric field distribution in the responder group. In an example embodiment, FIG. 12C depicts the estimated current density reaching the brain for responder (green), non-responder (red), optimized (blue) dosing. Dots represent the $95^{th}$ percentile of each distribution.

FIG. 12D shows the mean current density of tDCS non-responders with a fixed dose minus the tDCS responder mean. FIG. 12E shows the mean current density of tDCS non-responders with an optimized dose minus the tDCS responder mean. FIG. 12F shows a scatter plot of the voxel-wise mean current density of tDCS non-responders with optimized doses versus the voxel-wise mean current density of tDCS responders.

Computational models of current intensity and direction predicted treatment response with over 86% accuracy [92]. In an example embodiment, non-responders within the sample of tDCS recipients demonstrated 11.7% greater between-subject variability of current intensity and direction compared to tDCS responders. In another example embodiment, through GMM optimization, optimized electric field estimates of non-responders demonstrated a 61.7% reduction in between-subject variability and augmentation of average current density within the target brain regions (cf. FIG. 12A, g=0.98). Regression of the mean optimized current density map in the non-responder group demonstrated strong voxel-wise coherence (see FIG. 12F, $R^2$=0.693) with the target responder map. These optimized doses achieved an average treatment responder likelihood of 99.96%. The optimized doses of non-responder group were re-classified by the original SVM as responders with 100% accuracy.

The method disclosed herein is the provided to utilize MRI-derived computational models, machine learning, and dose optimization to maximize the likelihood of treatment response at an individual level. In some embodiments, features of MRI-derived electric field estimates successfully predicted working memory improvements with over 86% accuracy. In other embodiments, the feature weights of the SVM indicated that electrical current within the right and left superior frontal gyrus were the most essential for predicting treatment response [92]. With the whole-brain SVM weights, GMM optimization significantly improved the electric field profile to match tDCS responders compared to a conventional fixed dosing strategy by customizing tDCS parameters (by performing the method 250) for each individual to potentially increase the likelihood of treatment response of tDCS non-responders.

Leveraging these precision dosing techniques provides a tool to potentially address necessary questions for enhancing the efficacy of tDCS paired with CT for remediating cognitive decline in older adults. Therefore, the method disclosed herein provides critical information that can further improve existing prediction of tES current characteristics in older adults and a platform towards current dose customization for future tES applications in older adults.

The presented results demonstrate a novel, dose optimization paradigm for non-invasive electrical stimulation. Artificial intelligence combined with patient-specific MRI-based models of the head are utilized to determine the electrode positions and current intensities to optimize the induced electric field distribution that maximizes the likelihood of treatment response. It was shown that the optimal stimulation parameters reduce between-subject variability, elevated current intensity within targeted brain regions, and closely resembled the current distributions observed in treatment responders. Therefore, the method disclosed herein demonstrates the potential for a precision medicine model of non-invasive brain stimulation to flatten the trajectory of age-related working memory decline toward Alzheimer's disease.

3. Hardware Overview

FIG. 13 is a block diagram that illustrates a computer system 1300 upon which an embodiment of the invention may be implemented. Computer system 1300 includes a communication mechanism such as a bus 1310 for passing information between other internal and external components of the computer system 1300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1300, or a portion thereof, constitutes a means for performing one or more steps of one or more methods described herein.

A sequence of binary digits constitutes digital data that is used to represent a number or code for a character. A bus 1310 includes many parallel conductors of information so that information is transferred quickly among devices coupled to the bus 1310. One or more processors 1302 for processing information are coupled with the bus 1310. A processor 1302 performs a set of operations on information. The set of operations include bringing information in from the bus 1310 and placing information on the bus 1310. The set of operations also typically include comparing two or more units of information, shifting positions of units of information, and combining two or more units of information, such as by addition or multiplication. A sequence of operations to be executed by the processor 1302 constitutes computer instructions.

Computer system 1300 also includes a memory 1304 coupled to bus 1310. The memory 1304, such as a random-access memory (RAM) or other dynamic storage device, stores information including computer instructions. Dynamic memory allows information stored therein to be changed by the computer system 1300. RAM allows a unit of information stored at a location called a memory address to be stored and retrieved independently of information at neighboring addresses. The memory 1304 is also used by the processor 1302 to store temporary values during execution of computer instructions. The computer system 1300 also includes a read only memory (ROM) 1306 or other static storage device coupled to the bus 1310 for storing static information, including instructions, that is not changed by the computer system 1300. Also coupled to bus 1310 is a non-volatile (persistent) storage device 1308, such as a magnetic disk or optical disk, for storing information, including instructions, that persists even when the computer system 1300 is turned off or otherwise loses power.

Information, including instructions, is provided to the bus 1310 for use by the processor from an external input device

1312, such as a keyboard containing alphanumeric keys operated by a human user, or a sensor. A sensor detects conditions in its vicinity and transforms those detections into signals compatible with the signals used to represent information in computer system 1300. Other external devices coupled to bus 1310, used primarily for interacting with humans, include a display device 1314, such as a cathode ray tube (CRT) or a liquid crystal display (LCD), for presenting images, and a pointing device 1316, such as a mouse or a trackball or cursor direction keys, for controlling a position of a small cursor image presented on the display 1314 and issuing commands associated with graphical elements presented on the display 1314.

In the illustrated embodiment, special purpose hardware, such as an application specific integrated circuit (IC) 1320, is coupled to bus 1310. The special purpose hardware is configured to perform operations not performed by processor 1302 quickly enough for special purposes. Examples of application specific ICs include graphics accelerator cards for generating images for display 1314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1300 also includes one or more instances of a communications interface 1370 coupled to bus 1310. Communication interface 1370 provides a two-way communication coupling to a variety of external devices that operate with their own processors, such as printers, scanners, and external disks. In general, the coupling is with a network link 1378 that is connected to a local network 1380 to which a variety of external devices with their own processors are connected. For example, communication interface 1370 may be a parallel port or a serial port or a universal serial bus (USB) port on a personal computer. In some embodiments, communications interface 1370 is an integrated services digital network (ISDN) card or a digital subscriber line (DSL) card or a telephone modem that provides an information communication connection to a corresponding type of telephone line. In some embodiments, a communication interface 1370 is a cable modem that converts signals on bus 1310 into signals for a communication connection over a coaxial cable or into optical signals for a communication connection over a fiber optic cable. As another example, communications interface 1370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization, or other physical properties of carrier waves. For wireless links, the communications interface 1370 sends and receives electrical, acoustic, or electromagnetic signals, including infrared and optical signals, that carry information streams, such as digital data.

The term computer-readable medium is used herein to refer to any medium that participates in providing information to processor 1302, including instructions for execution. Such a medium may take many forms, including, but not limited to, non-volatile media, volatile media, and transmission media. Non-volatile media include, for example, optical or magnetic disks, such as storage device 1308. Volatile media include, for example, dynamic memory 1304. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1302, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1302, except for carrier waves and other signals.

Logic encoded in one or more tangible media includes one or both of processor instructions on a computer-readable storage media and special purpose hardware, such as ASIC *1320.

Network link 1378 typically provides information communication through one or more networks to other devices that use or process the information. For example, network link 1378 may provide a connection through local network 1380 to a host computer 1382 or to equipment 1384 operated by an Internet Service Provider (ISP). ISP equipment 1384 in turn provides data communication services through the public, world-wide packet-switching communication network of networks now commonly referred to as the Internet 1390. A computer called a server 1392 connected to the Internet provides a service in response to information received over the Internet. For example, server 1392 provides information representing video data for presentation at display 1314.

The invention is related to the use of computer system 1300 for implementing the techniques described herein. According to one embodiment of the invention, those techniques are performed by computer system 1300 in response to processor 1302 executing one or more sequences of one or more instructions contained in memory 1304. Such instructions, also called software and program code, may be read into memory 1304 from another computer-readable medium such as storage device 1308. Execution of the sequences of instructions contained in memory 1304 causes processor 1302 to perform the method steps described herein. In alternative embodiments, hardware, such as application specific integrated circuit 1320, may be used in place of or in combination with software to implement the invention. Thus, embodiments of the invention are not limited to any specific combination of hardware and software.

The signals transmitted over network link 1378 and other networks through communications interface 1370, carry information to and from computer system 1300. Computer system 1300 can send and receive information, including program code, through the networks 1380, 1390 among others, through network link 1378 and communications interface 1370. In an example using the Internet 1390, a server 1392 transmits program code for a particular application, requested by a message sent from computer 1300, through Internet 1390, ISP equipment 1384, local network 1380 and communications interface 1370. The received code may be executed by processor 1302 as it is received or may be stored in storage device 1308 or other non-volatile storage for later execution, or both. In this manner, computer system 1300 may obtain application program code in the form of a signal on a carrier wave.

Various forms of computer readable media may be involved in carrying one or more sequence of instructions or data or both to processor 1302 for execution. For example, instructions and data may initially be carried on a magnetic disk of a remote computer such as host 1382. The remote computer loads the instructions and data into its dynamic memory and sends the instructions and data over a telephone line using a modem. A modem local to the computer system 1300 receives the instructions and data on a telephone line and uses an infrared transmitter to convert the instructions and data to a signal on an infra-red a carrier wave serving as the network link 1378. An infrared detector serving as communications interface 1370 receives the instructions and data carried in the infrared signal and places information representing the instructions and data onto bus 1310. Bus 1310 carries the information to memory 1304 from which processor 1302 retrieves and executes the instructions using some of the data sent with the instructions. The instructions and data received in memory 1304 may optionally be stored on storage device 1308, either before or after execution by the processor 1302.

FIG. 14 illustrates a chip set 1400 upon which an embodiment of the invention may be implemented. Chip set 1400 is programmed to perform one or more steps of a method described herein and includes, for instance, the processor and memory components described with respect to FIG. 1A incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1400, or a portion thereof, constitutes a means for performing one or more steps of a method described herein.

In one embodiment, the chip set 1400 includes a communication mechanism such as a bus 1401 for passing information among the components of the chip set 1400. A processor 1403 has connectivity to the bus 1401 to execute instructions and process information stored in, for example, a memory 1405. The processor 1403 may include one or more processing cores with each core configured to perform independently. A multi-core processor enables multiprocessing within a single physical package. Examples of a multi-core processor include two, four, eight, or greater numbers of processing cores. Alternatively, or in addition, the processor 1403 may include one or more microprocessors configured in tandem via the bus 1401 to enable independent execution of instructions, pipelining, and multithreading. The processor 1403 may also be accompanied with one or more specialized components to perform certain processing functions and tasks such as one or more digital signal processors (DSP) 1407, or one or more application-specific integrated circuits (ASIC) 1409. A DSP 1407 typically is configured to process real-world signals (e.g., sound) in real time independently of the processor 1403. Similarly, an ASIC 1409 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1403 and accompanying components have connectivity to the memory 1405 via the bus 1401. The memory 1405 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1405 also stores the data associated with or generated by the execution of one or more steps of the methods described herein.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the items, elements, or steps modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

4. References

[1] Knotkova H, Nitsche M A, Bikson M, Woods A J, editors. Practical Guide to Transcranial Direct Current Stimulation. Cham: Springer International Publishing; 2019. https://doi.org/10.1007/978-3-319-95948-1.

[2] Woods A J, Antal A, Bikson M, Boggio P S, Brunoni A R, Celnik P, et al. A technical guide to tDCS, and related non-invasive brain stimulation tools. Clin Neurophysiol 2016; 127:1031-48. https://doi.org/10.1016/j.clinph.2015.11.012.

[3] Bikson M, Grossman P, Thomas C, Zannou A L, Jiang J, Adnan T, et al. Safety of Transcranial Direct Current Stimulation: Evidence Based Update 2016. Brain Stimul 2016. https://doi.org/10.1016/j.brs.2016.06.004.

[4] Nitsche M A, Cohen L G, Wassermann E M, Priori A, Lang N, Antal A, et al. Transcranial direct current stimulation: State of the art 2008. Brain Stimul 2008. https://doi.org/10.1016/j.brs.2008.06.004.

[5] Albizu A, Indahlastari A, Woods A J. Non-invasive Brain Stimulation—Encyclopedia of Gerontology and Population Aging. In: Gu D, Dupre M E, editors., Cham: Springer International Publishing; 2019, p. 1-8. https://doi.org/10.1007/978-3-319-69892-2_682-1.

[6] Rosen A C, Ramkumar M, Nguyen T, Hoeft F. Noninvasive transcranial brain stimulation and pain. Curr Pain Headache Rep 2009. https://doi.org/10.1007/s11916-009-0004-2.

[7] Clancy K J, Baisley S K, Albizu A, Kartvelishvili N, Ding M, Li W. Lasting connectivity increase and anxiety reduction via transcranial alternating current stimulation. Soc Cogn Affect Neurosci 2018; 13:1305-16. https://doi.org/10.1093/scan/nsy096.

[8] Chhatbar P Y, Ramakrishnan V, Kautz S, George M S, Adams R J, Feng W. Transcranial Direct Current Stimulation Post-Stroke Upper Extremity Motor Recovery Studies Exhibit a Dose-Response Relationship. Brain Stimul 2016. https://doi.org/10.1016/j.brs.2015.09.002.

[9] Datta A, Baker J M, Bikson M, Fridriksson J. Individualized model predicts brain current flow during transcranial direct-current stimulation treatment in responsive stroke patient. Brain Stimul 2011. https://doi.org/10.1016/j.brs.2010.11.001.

[10] Bikson M, Truong D Q, Mourdoukoutas A P, Aboseria M, Khadka N, Adair D, et al. Modeling sequence and quasi-uniform assumption in computational neurostimulation. Prog. Brain Res., 2015. https://doi.org/10.1016/bs.pbr.2015.08.005.

[11] Ranieri F, Podda M V., Riccardi E, Frisullo G, Dileone M, Profice P, et al. Modulation of LTP at rat hippocampal CA3-CA1 synapses by direct current stimulation. J Neurophysiol 2012. https://doi.org/10.1152/jn.00319.2011.

[12] Fritsch B, Reis J, Martinowich K, Schambra H M, Ji Y, Cohen L G, et al. Direct current stimulation promotes BDNF-dependent synaptic plasticity: Potential implications for motor learning. Neuron 2010. https://doi.org/10.1016/j.neuron.2010.03.035.

[13] Artola A, Bröcher S, Singer W. Different voltage-dependent thresholds for inducing long-term depression and long-term potentiation in slices of rat visual cortex. Nature 1990. https://doi.org/10.1038/347069a0.

[14] Kronberg G, Bridi M, Abel T, Bikson M, Parra L C. Direct Current Stimulation Modulates LTP and LTD: Activity Dependence and Dendritic Effects. Brain Stimul 2017. https://doi.org/10.1016/j.brs.2016.10.001.

[15] Kronberg G, Rahman A, Sharma M, Bikson M, Parra L C. Direct current stimulation boosts hebbian plasticity in vitro. Brain Stimul 2020. https://doi.org/10.1016/j.brs.2019.10.014.

[16] Márquez-Ruiz J, Leal-Campanario R, Sanchez-Campusano R, Molaee-Ardekani B, Wendling F, Miranda P C, et al. Transcranial direct-current stimulation modulates synaptic mechanisms involved in associative learning in behaving rabbits. Proc Natl Acad Sci USA 2012. https://doi.org/10.1073/pnas.1121147109.

[17] Podda M V, Cocco S, Mastrodonato A, Fusco S, Leone L, Barbati S A, et al. Anodal transcranial direct current stimulation boosts synaptic plasticity and memory in mice via epigenetic regulation of Bdnf expression. Sci Rep 2016. https://doi.org/10.1038/srep22180.

[18] Nitsche M A, Paulus W. Excitability changes induced in the human motor cortex by weak transcranial direct current stimulation. J Physiol 2000. https://doi.org/10.1111/j.1469-7793.2000.t01-1-00633.x.

[19] Hoy K E, Arnold S L, Emonson M R L, Daskalakis Z J, Fitzgerald P B. An investigation into the effects of tDCS dose on cognitive performance over time in patients with schizophrenia. Schizophr Res 2014. https://doi.org/10.1016/j.schres.2014.03.006.

[20] Esmaeilpour Z, Marangolo P, Hampstead B M, Bestmann S, Galletta E, Knotkova H, et al. Incomplete evidence that increasing current intensity of tDCS boosts outcomes. Brain Stimul 2018. https://doi.org/10.1016/j.brs.2017.12.002.

[21] Woods A J, Bryant V, Sacchetti D, Gervits F, Hamilton R. Effects of electrode drift in transcranial direct current stimulation. Brain Stimul 2015. https://doi.org/10.1016/j.brs.2014.12.007.

[22] Opitz A, Yeagle E, Thielscher A, Schroeder C, Mehta A D, Milham M P. On the importance of precise electrode placement for targeted transcranial electric stimulation. Neuroimage 2018; 181:560-7. https://doi.org/10.1016/j.neuroimage.2018.07.027.

[23] Radman T, Ramos R L, Brumberg J C, Bikson M. Role of cortical cell type and morphology in subthreshold and suprathreshold uniform electric field stimulation in vitro. Brain Stimul 2009. https://doi.org/10.1016/j.brs.2009.03.007.

[24] Jacobson L, Koslowsky M, Lavidor M. TDCS polarity effects in motor and cognitive domains: A meta-analytical review. Exp Brain Res 2012. https://doi.org/10.1007/s00221-011-2891-9.

[25] Rawji V, Ciocca M, Zacharia A, Soares D, Truong D, Bikson M, et al. tDCS changes in motor excitability are specific to orientation of current flow. Brain Stimul 2018. https://doi.org/10.1016/j.brs.2017.11.001.

[26] Indahlastari A, Albizu A, Nissim N R, Traeger K R, O'Shea A, Woods A J. Methods to monitor accurate and consistent electrode placements in conventional transcranial electrical stimulation. Brain Stimul 2019; 12:267-74. https://doi.org/10.1016/j.brs.2018.10.016.

[27] Thomas C, Datta A, Woods A. Effect of Aging on Cortical Current Flow Due to Transcranial Direct Current Stimulation: Considerations for Safety. Proc. Annu. Int. Conf. IEEE Eng. Med. Biol. Soc. EMBS, 2018. https://doi.org/10.1109/EMBC.2018.8513014.

[28] Indahlastari A, Albizu A, O'Shea A, Forbes M A, Nissim N R, Kraft J N, et al. Modeling Transcranial Electrical Stimulation in the Aging Brain. Brain Stimul 2020; 13. https://doi.org/10.1016/j.brs.2020.02.007.

[29] Datta A, Bansal V, Diaz J, Patel J, Reato D, Bikson M. Gyri-precise head model of transcranial direct current stimulation: Improved spatial focality using a ring electrode versus conventional rectangular pad. Brain Stimul 2009. https://doi.org/10.1016/j.brs.2009.03.005.

[30] Truong D Q, Magerowski G, Blackburn G L, Bikson M, Alonso-Alonso M. Computational modeling of transcranial direct current stimulation (tDCS) in obesity: Impact of head fat and dose guidelines. NeuroImage Clin 2013. https://doi.org/10.1016/j.nicl.2013.05.011.

[31] Kessler S K, Minhas P, Woods A J, Rosen A, Gorman C, Bikson M. Dosage Considerations for Transcranial Direct Current Stimulation in Children: A Computational Modeling Study. PLoS One 2013. https://doi.org/10.1371/journal.pone.0076112.

[32] Minhas P, Bikson M, Woods A J, Rosen A R, Kessler S K. Transcranial direct current stimulation in pediatric brain: A computational modeling study. Proc. Annu. Int. Conf. IEEE Eng. Med. Biol. Soc. EMBS, 2012. https://doi.org/10.1109/EMBC.2012.6346067.

[33] Huang Y, Datta A, Bikson M, Parra L C. Realistic vOlumetric-Approach to Simulate Transcranial Electric Stimulation—ROAST—a fully automated open-source pipeline. J Neural Eng 2019. https://doi.org/10.1088/1741-2552/ab208d.

[34] Windhoff M, Opitz A, Thielscher A. Electric field calculations in brain stimulation based on finite elements: An optimized processing pipeline for the generation and usage of accurate individual head models. Hum Brain Mapp 2013. https://doi.org/10.1002/hbm.21479.

[35] Kasinadhuni A K, Indahlastari A, Chauhan M, Schär M, Mareci T H, Sadleir R J. Imaging of current flow in the human head during transcranial electrical therapy. Brain Stimul 2017; 10:764-72. https://doi.org/10.1016/j.brs.2017.04.125.

[36] Göksu C, Hanson L G, Siebner H R, Ehses P, Scheffler K, Thielscher A. Human in-vivo brain magnetic resonance current density imaging (MRCDI). Neuroimage 2018. https://doi.org/10.1016/j.neuroimage.2017.12.075.

[37] Huang Y, Liu A A, Lafon B, Friedman D, Dayan M, Wang X, et al. Measurements and models of electric fields in the in vivo human brain during transcranial electric stimulation. Elife 2017. https://doi.org/10.7554/eLife.18834.

[38] Indahlastari A, Kasinadhuni A K, Saar C, Castellano K, Mousa B, Chauhan M, et al. Methods to compare predicted and observed phosphene experience in TACS subjects. Neural Plast 2018. https://doi.org/10.1155/2018/8525706.

[39] Suen P J C, Doll S, Batistuzzo M C, Busatto G, Razza L B, Padberg F, et al. Association between tDCS computational modeling and clinical outcomes in depression: data from the ELECT-TDCS trial. Eur Arch Psychiatry Clin Neurosci 2020. https://doi.org/10.1007/s00406-020-01127-w.

[40] Antonenko D, Thielscher A, Saturnino G B, Aydin S, Ittermann B, Grittner U, et al. Towards precise brain stimulation: Is electric field simulation related to neuromodulation? Brain Stimul 2019. https://doi.org/10.1016/j.brs.2019.03.072.

[41] Chang C C, Lin C J. LIBSVM: A Library for support vector machines. ACM Trans Intell Syst Technol 2011. https://doi.org/10.1145/1961189.1961199.

[42] Mwangi B, Tian T S, Soares J C. A review of feature reduction techniques in Neuroimaging. Neuroinformatics 2014. https://doi.org/10.1007/s12021-013-9204-3.

[43] Dubois J, Galdi P, Han Y, Paul L K, Adolphs R. Resting-State Functional Brain Connectivity Best Predicts the Personality Dimension of Openness to Experience. Personal Neurosci 2018. https://doi.org/10.1017/pen.2018.8.

[44] Kashyap R, Kong R, Bhattacharjee S, Li J, Zhou J, Thomas Yeo B T. Individual-specific fMRI-Subspaces improve functional connectivity prediction of behavior. Neuroimage 2019. https://doi.org/10.1016/j.neuroimage.2019.01.069.

[45] Mercer J. XVI. Functions of positive and negative type, and their connection the theory of integral equations. Philos Trans R Soc London Ser A, Contain Pap a Math or Phys Character 1909. https://doi.org/10.1098/rsta.1909.0016.

[46] I. Guyon, B. Boser, V. Vapnik. Automatic Capacity Tuning of Very Large VC-Dimension Classifiers. Adv Neural Inf Process Syst 1993.

[47] Li J, Kong R, Liégeois R, Orban C, Tan Y, Sun N, et al. Global signal regression strengthens association between resting-state functional connectivity and behavior. Neuroimage 2019. https://doi.org/10.1016/j.neuroimage.2019.04.016.

[48] Kambeitz J, Goerigk S, Gattaz W, Falkai P, Benseñor I M, Lotufo P A, et al. Clinical patterns differentially predict response to transcranial direct current stimulation (tDCS) and escitalopram in major depression: A machine learning analysis of the ELECT-TDCS study. J Affect Disord 2020. https://doi.org/10.1016/j.jad.2020.01.118.

[49] Nissim N R, O'Shea A, Indahlastari A, Kraft J N, von Mering O, Aksu S, et al. Effects of Transcranial Direct Current Stimulation Paired With Cognitive Training on Functional Connectivity of the Working Memory Network in Older Adults. Front Aging Neurosci 2019. https://doi.org/10.3389/fnagi.2019.00340.

[50] Li X, Morgan P S, Ashburner J, Smith J, Rorden C. The first step for neuroimaging data analysis: DICOM to NIfTI conversion. J Neurosci Methods 2016. https://doi.org/10.1016/j.jneumeth.2016.03.001.

[51] Morey R A, Petty C M, Xu Y, Pannu Hayes J, Wagner H R, Lewis D V., et al. A comparison of automated segmentation and manual tracing for quantifying hippocampal and amygdala volumes. Neuroimage 2009. https://doi.org/10.1016/j.neuroimage.2008.12.033.

[52] Cardinale F, Chinnici G, Bramerio M, Mai R, Sartori I, Cossu M, et al. Validation of FreeSurfer-Estimated Brain Cortical Thickness: Comparison with Histologic Measurements. Neuroinformatics 2014. https://doi.org/10.1007/s12021-014-9229-2.

[53] Qianqian Fang, Boas D A. Tetrahedral mesh generation from volumetric binary and grayscale images. 2009 IEEE Int. Symp. Biomed. Imaging From Nano to Macro, IEEE; 2009, p. 1142-5. https://doi.org/10.1109/ISBI.2009.5193259.

[54] Dular P, Geuzaine C, Henrotte F, Legros W. A general environment for the treatment of discrete problems and its application to the finite element method. IEEE Trans Magn 1998. https://doi.org/10.1109/20.717798.

[55] Huang Y, Dmochowski J P, Su Y, Datta A, Rorden C, Parra L C. Automated MRI segmentation for individualized modeling of current flow in the human head. J Neural Eng 2013. https://doi.org/10.1088/1741-2560/10/6/066004.

[56] Ashburner J. A fast diffeomorphic image registration algorithm. Neuroimage 2007. https://doi.org/10.1016/j.neuroimage.2007.07.007.

[57] Saeys Y, Inza I, Larrañaga P. A review of feature selection techniques in bioinformatics. Bioinformatics 2007. https://doi.org/10.1093/bioinformatics/btm344.

[58] Iguyon I, Elisseeff A. An introduction to variable and feature selection. J Mach Learn Res 2003. https://doi.org/10.1162/153244303322753616.

[59] Steinwart I, Christmann A. Support Vector Machines. Springer Science & Business Media; 2008.

[60] Varoquaux G, Raamana P R, Engemann D A, Hoyos-Idrobo A, Schwartz Y, Thirion B. Assessing and tuning brain decoders: Cross-validation, caveats, and guidelines. Neuroimage 2017. https://doi.org/10.1016/j.neuroimage.2016.10.038.

[61] Polosecki P, Castro E, Rish I, Pustina D, Warner J H, Wood A, et al. Resting-state connectivity stratifies premanifest Huntington's disease by longitudinal cognitive decline rate. Sci Rep 2020. https://doi.org/10.1038/s41598-020-58074-8.

[62] Lindquist M A, Krishnan A, López-Solà M, Jepma M, Woo C W, Koban L, et al. Group-regularized individual prediction: theory and application to pain. Neuroimage 2017. https://doi.org/10.1016/j.neuroimage.2015.10.074.

[63] Cole J H, Leech R, Sharp D J. Prediction of brain age suggests accelerated atrophy after traumatic brain injury. Ann Neurol 2015. https://doi.org/10.1002/ana.24367.

[64] Goldstein J M, Seidman L J, Makris N, Ahern T, O'Brien L M, Caviness V S, et al. Hypothalamic Abnormalities in Schizophrenia: Sex Effects and Genetic Vulnerability. Biol Psychiatry 2007. https://doi.org/10.1016/j.biopsych.2006.06.027.

[65] Mathworks. Statistics and Machine Learning Toolbox™ User's Guide R2019b. MatLab 2019.

[66] Hedges L V. Distribution Theory for Glass's Estimator of Effect Size and Related Estimators. J Educ Stat 1981. https://doi.org/10.2307/1164588.

[67] Smirnov N. Table for Estimating the Goodness of Fit of Empirical Distributions. Ann Math Stat 1948. https://doi.org/10.1214/aoms/1177730256.

[68] Massey F J. The Kolmogorov-Smirnov Test for Goodness of Fit. J Am Stat Assoc 1951. https://doi.org/10.1080/01621459.1951.10500769.

[69] Fawcett T. ROC graphs: Notes and practical considerations for researchers. Mach Learn 2004.

[70] Mosayebi Samani M, Agboada D, Jamil A, Kuo M F, Nitsche M A. Titrating the neuroplastic effects of cathodal transcranial direct current stimulation (tDCS) over the primary motor cortex. Cortex 2019. https://doi.org/10.1016/j.cortex.2019.04.016.

[71] Ramaraju S, Roula M A, McCarthy P W. Modelling the effect of electrode displacement on transcranial direct current stimulation (tDCS). J Neural Eng 2018. https://doi.org/10.1088/1741-2552/aa8d8a.

[72] Thomas Yeo B T, Krienen F M, Sepulcre J, Sabuncu M R, Lashkari D, Hollinshead M, et al. The organization of the human cerebral cortex estimated by intrinsic functional connectivity. J Neurophysiol 2011. https://doi.org/10.1152/jn.00338.2011.

[73] D'Esposito M, Postle B R, Ballard D, Lease J. Maintenance versus manipulation of information held in working memory: An event-related fMRI study. Brain Cogn 1999. https://doi.org/10.1006/brcg.1999.1096.

[74] Petrides M. Dissociable roles of mid-dorsolateral prefrontal and anterior inferotemporal cortex visual working memory. J Neurosci 2000. https://doi.org/10.1523/JNEUROSCI.20-19-07496.2000.

[75] Blumenfeld R S, Nomura E M, Gratton C, D'Esposito M. Lateral prefrontal cortex is organized into parallel dorsal and ventral streams along the rostro-caudal axis. Cereb Cortex 2013. https://doi.org/10.1093/cercor/bhs223.

[76] Nissim N R, O'Shea A, Indahlastari A, Telles R, Richards L, Porges E, et al. Effects of in-Scanner Bilateral Frontal tDCS on Functional Connectivity of the Working Memory Network in Older Adults. Front Aging Neurosci 2019. https://doi.org/10.3389/fnagi.2019.00051.

[77] Packard M G, Knowlton B J. Learning and Memory Functions of the Basal Ganglia. Annu Rev Neurosci 2002. https://doi.org/10.1146/annurev.neuro.25.112701.142937.

[78] McNab F, Klingberg T. Prefrontal cortex and basal ganglia control access to working memory. Nat Neurosci 2008. https://doi.org/10.1038/nn2024.

[79] Hausman H K, O'Shea A, Kraft J N, Boutzoukas E M, Evangelista N D, Van Etten E J, et al. The Role of Resting-State Network Functional Connectivity in Cognitive Aging. Front Aging Neurosci 2020. https://doi.org/10.3389/fnagi.2020.00177.

[80] Clancy K J, Albizu A, Schmidt N B, Li W. Intrinsic sensory disinhibition contributes to intrusive re-experiencing in combat veterans. Sci Rep 2020; 10:936. https://doi.org/10.1038/s41598-020-57963-2.

[81] Szymkowicz S M, McLaren M E, Suryadevara U, Woods A J. Transcranial direct current stimulation use in the treatment of neuropsychiatric disorders: A brief review. Psychiatr Ann 2016. https://doi.org/10.3928/00485713-20161006-01.

[82] Woods A J, Cohen R, Marsiske M, Alexander G E, Czaja S J, Wu S. Augmenting cognitive training in older adults (The ACT Study): Design and Methods of a Phase III tDCS and cognitive training trial. Contemp Clin Trials 2018; 65:19-32. https://doi.org/10.1016/j.cct.2017.11.017.

[83] McCann, H., Pisano, G., & Beltrachini, L. (2019). Variation in reported human head tissue electrical conductivity values. Brain topography, 32(5), 825-858.

[84] Gabriel, S., Lau, R. W., & Gabriel, C. (1996). The dielectric properties of biological tissues: II. Measurements in the frequency range 10 Hz to 20 GHz. Physics in medicine & biology, 41(11), 2251.

[85] Indahlastari A, Albizu A, Nissim N R, Traeger K R, O'Shea A, Woods A J. Methods to monitor accurate and consistent electrode placements in conventional transcranial electrical stimulation. Brain Stimul 2019; 12:267-74. https://doi.org/10.1016/j.brs.2018.10.016.

[86] Oostenveld R, Praamstra P. The five percent electrode system for high-resolution EEG and ERP measurements. Clin Neurophysiol 2001; 112:713-9. https://doi.org/10.1016/S1388-2457(00)00527-7.

[87] Dmochowski J P, Datta A, Huang Y, Richardson J D, Bikson M, Fridriksson J, et al. Targeted transcranial direct current stimulation for rehabilitation after stroke. Neuroimage 2013; 75:12-9. https://doi.org/10.1016/j.neuroimage.2013.02.049.

[88] Huang Y, Thomas C, Datta A, Parra L C. Optimized tDCS for Targeting Multiple Brain Regions: An Integrated Implementation*. n.d.

[89] Dmochowski J P, Bikson M, Parra L C. The Point Spread Function of the Human Head and its Implications for Transcranial Current Stimulation. n.d.

[90] Dmochowski J P, Datta A, Bikson M, Su Y, Parra L C. Optimized multi-electrode stimulation increases focality and intensity at target. J. Neural Eng., vol. 8, IOP Publishing; 2011, p. 046011. https://doi.org/10.1088/1741-2560/8/4/046011.

[91] Nissim N R, O'Shea A, Indahlastari A, Kraft J N, von Mering O, Aksu S, et al. Effects of Transcranial Direct Current Stimulation Paired With Cognitive Training on Functional Connectivity of the Working Memory Network in Older Adults. Front Aging Neurosci 2019; 11:340. https://doi.org/10.3389/fnagi.2019.00340.

[92] Albizu A, Fang R, Indahlastari A, O'Shea A, Stolte S E, See K B, et al. Machine learning and individual variability in electric field characteristics predict tDCS treatment response. Brain Stimul 2020. https://doi.org/10.1016/j.brs.2020.10.001.

[93] Huang Y, Datta A, Bikson M, Parra L C. Realistic vOlumetric-Approach to Simulate Transcranial Electric Stimulation—ROAST—a fully automated open-source pipeline. J Neural Eng 2019. https://doi.org/10.1088/1741-2552/ab208d.

What is claimed is:

1. A method comprising:

determining a location of each voxel of a plurality of voxels in a reference frame of an electro-stimulation device that comprises a plurality of electrodes positioned on a head of a subject;

obtaining measurements that indicate a tissue type at each voxel inside the head of the subject based on an imaging device;

determining, with a processor, a value of one or more parameters of the electro-stimulation device of an electric field to improve a cognitive function of the subject;

wherein the value of the one or more parameters is determined per target voxel of the plurality of voxels based on the tissue type measurement of each target voxel to ensure respective target dose values are received at the respective target voxels; and wherein the target voxels and the respective target dose values at the target voxels are associated with a greater improvement in the cognitive function than other voxels of the plurality of voxels and other dose values of the one or more parameters of the electric field.

2. The method as recited in claim 1, wherein the value of the parameter of the electro-stimulation device is a plurality of locations of the plurality of electrodes on the head.

3. The method as recited in claim 2, wherein the plurality of electrodes comprises an anode electrode and a cathode electrode and wherein the plurality of locations include T3 and T4 of the 10-20 system.

4. The method as recited in claim 1, wherein the value of the parameter of the electro-stimulation device is an amplitude of an electric current applied by the plurality of electrodes.

5. The method as recited in claim 4, wherein the amplitude of the electric current is selected within a range from about 1 mA to about 3 mA.

6. The method as recited in claim 1, wherein the value of the parameter of the electro-stimulation device is a plurality of locations of the plurality of electrodes on the head and an amplitude of an electric current applied by the plurality of electrodes.

7. The method as recited in claim 1, wherein the respective target dose value of the parameter of the electric field is a direction of the electric field at each target voxel.

8. The method as recited in claim 1, wherein the respective target dose value of the parameter of the electric field is an intensity of the electric field at each target voxel.

9. The method as recited in claim 1, wherein the respective target dose value of the parameter of the electric field is a direction of the electric field at each target voxel and an intensity of the electric field at each target voxel.

10. The method as recited in claim 1, further comprising:

configuring the electro-stimulation device to generate the determined value of the one or more parameters of the electro-stimulation device; and generating, with the configured electro-stimulation device, the electric field with the respective target values of the one or more parameters at each target voxel.

11. The method as recited in claim 1, further comprising:

a) performing the obtaining step for a plurality of subjects;

b) generating, with the electro-stimulation device, an electric field at each voxel inside the head of each subject based on a test value of the one or more parameters of the electro-stimulation device;

c) determining, with the processor, a test value of the one or more parameters of the electric field generated at each voxel inside the head of each subject based on the tissue type measurements and the test value of the one or more parameters of the electro-stimulation device;

d) assessing the cognitive function of each subject before and after the generating step;

e) classifying the plurality of subjects into a first group of subjects and a second group of subjects based on the assessing step; and f) determining the target voxels and the respective target dose values of the one or more parameters of the electric field for the target voxels based on the test value of the one or more parameters of the electric field generated at each voxel inside the head of the first group of subjects.

12. The method as recited in claim 11, wherein the determining the test value of the one or more parameters comprises determining the test value of one or more first parameters of the electric field;

and wherein the determining the target voxels and the respective target dose values of the one or more parameters comprises selecting one or more second parameters among the one or more first parameters of the electric field such that the test value of the one or more second parameters distinguishes the first group of subjects from the second group of subjects.

13. The method as recited in claim 11, wherein the first group of subjects are classified based on the assessing step indicating a larger improvement in the cognitive function before and after the generating step relative to the second group of subjects.

14. The method as recited in claim 11, wherein steps a)-c) are performed multiple times for each subject and wherein step f) comprises determining a mean of the test value of the one or more parameters of the electric field over the multiple times for each subject among the first group of subjects.

15. The method as recited in claim 14, further comprising determining, with the processor, a relative weight of contribution of the test value of the one or more parameters at each voxel to the classifying the first group of subjects.

16. The method as recited in claim 1, wherein the determining of the value of one or more parameters of the electro-stimulation device is based on tissue conductivity of the tissue type measurements at each voxel.

17. The method as recited in claim 12, further comprising:
generating pre-field current density maps of the head of each subject during a test taken before generating the electric field and generating post-field current density maps of the head of each subject during a test taken after generating the electric field; and
using artificial intelligence to identify the target voxels and to identify the most effective stimulation parameters by comparing the pre-field current density maps with the post-field current density maps.

18. A system comprising:
an electro-stimulation device comprising a plurality of electrodes;
at least one processor; and
at least one memory including one or more sequences of instructions;
the at least one memory and the one or more sequence of instructions configured to, with the at least one processor, cause the system;
to determine a location of each voxel of a plurality of voxels in a reference frame of the electro-stimulation device positioned on a head of a subject;
to obtain measurements that indicate a tissue type at each voxel inside the head of the subject based on an imaging device;
to determine a value of one or more parameters of the electro-stimulation device;
to generate an electric field via the electro-stimulation device based on the value of the one or more parameters of an electric field to improve a cognitive function of the subject;
wherein the value of the one or more parameters is determined per target voxel based on the tissue type measurement of each target voxel to ensure respective target dose values are received at the respective target voxels; and
wherein the target voxels and the respective target dose values at the target voxels are associated with a greater improvement in cognitive function than other voxels of the plurality of voxels and other dose values of the one or more parameters of the electric field.

19. The system as recited in claim 18, further comprising the imaging device; wherein the memory and the sequences of instructions are configured to cause the system;

to measure the measurements that indicate the tissue type at each voxel with the imaging device; and
to transmit a signal indicating the measurements from the imaging device to the processor.

20. The system as recited in claim 18, further comprising a power supply configured to supply electrical power to the plurality of electrodes and wherein the power supply is communicatively coupled with the processor.

21. The system as recited in claim 20, wherein the value of the one or more parameters of the electro-stimulation device is an amplitude of a current intensity supplied to the electrodes;
wherein the memory and the sequences of instructions are configured to cause the processor to transmit a first signal to the power supply such that electrical power is provided to the electrodes such that the amplitude of the current intensity is supplied to the electrodes.

22. The system as recited in claim 18 wherein the imaging device is one of an X-ray Computed tomography (CT) scanner, a nuclear magnetic resonance imagery (MRI) scanner or a four-dimensional computed tomography (4DCT) based ventilation imaging system;
wherein the electro-stimulation device is
(i) a transcranial direct current stimulation computed tomography (tDCS-CT) scanner, or
(ii) one of a transcranial magnetic stimulation device, an electroconvulsive therapy device, a deep brain stimulation device, a transcranial alternative current device, or a transcranial random noise stimulation device.

23. A method comprising:
determining a location of each voxel of a plurality of voxels in a reference frame of an electro-stimulation device that comprises a plurality of electrodes positioned on a head of a subject;
obtaining measurements that indicate a tissue type at each voxel inside the head of the subject based on an imaging device;
determining, with a processor, a value of one or more parameters of the electro-stimulation device based on the tissue type measurements at each voxel such that the electro-stimulation device is configured to generate respective target dose values of one or more parameters of an electric field at target voxels of the plurality of voxels inside the head of the subject to improve a cognitive function of the subject;
wherein the target voxels and the respective target dose values at the target voxels are associated with a greater improvement in the cognitive function than other voxels of the plurality of voxels and other dose values of the one or more parameters of the electric field;
wherein the method further comprises:
a) performing the obtaining step for a plurality of subjects;
b) generating, with the electro-stimulation device, an electric field at each voxel inside the head of each subject based a test value of the one or more parameters of the electro-stimulation device;
c) determining, with the processor, a test value of the one or more parameters of the electric field generated at each voxel inside the head of each subject based on the tissue type measurements and the test value of the one or more parameters of the electro-stimulation device;
d) assessing the cognitive function of each subject before and after the generating step;

e) classifying the plurality of subjects into a first group of subjects and a second group of subjects based on the assessing step; and f) determining the target voxels and the respective target dose values of the one or more parameters of the electric field for the target voxels based on the test value of the one or more parameters of the electric field generated at each voxel inside the head of the first group of subjects;

wherein the determining the test value of the one or more parameters comprises determining the test value of one or more first parameters of the electric field;

wherein the determining the target voxels and the respective target dose values of the one or more parameters comprises selecting one or more second parameters among the one or more first parameters of the electric field such that the test value of the one or more second parameters distinguishes the first group of subjects from the second group of subjects;

wherein the method further comprises:

generating pre-field current density maps of the head of each subject during a test taken before generating the electric field and generating post-field current density maps of the head of each subject during a test taken after generating the electric field; and using artificial intelligence to identify the target voxels and to identify the most effective stimulation parameters by comparing the pre-field current density maps with the post-field current density maps.

24. A method comprising:

obtaining measurements that indicate a tissue type at each voxel inside a head of a each subject of a plurality of subjects based on an imaging device;

generating, with an electro-stimulation device, an electric field at each voxel inside the head of each subject based on a test value of the one or more parameters of the electro-stimulation device;

determining, with the processor, a test value of the one or more parameters of the electric field generated at each voxel inside the head of each subject based on the tissue type measurements and the test value of the one or more parameters of the electro-stimulation device;

assessing the cognitive function of each subject before and after the generating step;

classifying the plurality of subjects into a first group of subjects and a second group of subjects based on the assessing step;

determining target voxels and respective target dose values of the one or more parameters of the electric field for the target voxels based on the test value of the one or more parameters of the electric field generated at each voxel inside the head of the first group of subjects;

wherein the determining the test value of the one or more parameters comprises determining the test value of one or more first parameters of the electric field;

wherein the determining the target voxels and the respective target dose values of the one or more parameters comprises selecting one or more second parameters among the one or more first parameters of the electric field such that the test value of the one or more second parameters distinguishes the first group of subjects from the second group of subjects;

generating pre-field current density maps of the head of each subject during a test taken before generating the electric field and generating post-field current density maps of the head of each subject during a test taken after generating the electric field; and using artificial intelligence to identify the target voxels and to identify the most effective stimulation parameters by comparing the pre-field current density maps with the post-field current density maps.

* * * * *